US012576051B2

(12) United States Patent
Dohil et al.

(10) Patent No.: US 12,576,051 B2
(45) Date of Patent: *Mar. 17, 2026

(54) METHODS AND COMPOSITION FOR TREATING RESPIRATORY OBSTRUCTIVE DISEASES

(71) Applicant: The Regents of the University of California, Oakland, CA (US)

(72) Inventors: Ranjan Dohil, San Diego, CA (US); Guillermo Flores-Delgado, Oceanside, CA (US)

(73) Assignee: The Regents of the University of California, Oakland, CA (US)

( * ) Notice: Subject to any disclaimer, the term of this patent is extended or adjusted under 35 U.S.C. 154(b) by 1023 days.

This patent is subject to a terminal disclaimer.

(21) Appl. No.: 17/630,758

(22) PCT Filed: Jul. 30, 2020

(86) PCT No.: PCT/US2020/044204
§ 371 (c)(1),
(2) Date: Jan. 27, 2022

(87) PCT Pub. No.: WO2021/022012
PCT Pub. Date: Feb. 4, 2021

(65) Prior Publication Data

US 2022/0265583 A1 Aug. 25, 2022

Related U.S. Application Data

(60) Provisional application No. 62/880,620, filed on Jul. 30, 2019.

(51) Int. Cl.
*A61K 31/145* (2006.01)
*A61K 9/00* (2006.01)
*A61P 11/12* (2006.01)

(52) U.S. Cl.
CPC .......... *A61K 31/145* (2013.01); *A61K 9/0078* (2013.01); *A61P 11/12* (2018.01)

(58) Field of Classification Search
CPC .... A61K 31/145; A61K 45/06; A61K 9/0078; A61P 11/02; A61P 11/12; A61P 31/04
See application file for complete search history.

(56) References Cited

U.S. PATENT DOCUMENTS

| | | | | | |
|---|---|---|---|---|---|
| 6,221,335 | B1 * | 4/2001 | Foster | C07B 59/002 | 424/1.81 |
| 6,440,710 | B1 * | 8/2002 | Keinan | C12P 13/02 | 435/188.5 |
| 6,603,008 | B1 * | 8/2003 | Ando | A61P 7/04 | 546/271.4 |
| 7,517,990 | B2 * | 4/2009 | Ito | C07D 233/56 | 546/184 |
| 2004/0024356 | A1 | 2/2004 | Tanaka | | |
| 2005/0107420 | A1 * | 5/2005 | Armstrong | A61K 31/439 | 514/292 |
| 2007/0082929 | A1 * | 4/2007 | Gant | A61P 43/00 | 546/273.7 |
| 2007/0197695 | A1 * | 8/2007 | Potyen | C08K 5/55 | 524/110 |
| 2014/0073694 | A1 * | 3/2014 | Cicchetti | A61P 43/00 | 514/665 |
| 2014/0322315 | A1 | 10/2014 | Dohil et al. | | |
| 2014/0357592 | A1 | 12/2014 | O'Neil et al. | | |
| 2016/0106689 | A1 * | 4/2016 | O'Neil | A61K 45/06 | 514/2.6 |
| 2017/0362187 | A1 | 12/2017 | Johnson | | |
| 2018/0147190 | A1 | 5/2018 | McCarty et al. | | |

FOREIGN PATENT DOCUMENTS

| | | | |
|---|---|---|---|
| WO | 2005/037245 A2 | | 4/2005 |
| WO | WO 2020198529 | * | 3/2019 |

OTHER PUBLICATIONS

Dyck et al. (Journal of Neurochemistry, 1986, vol. 46 Issue 2, pp. 399-404) (Year: 1986).*
Wolen et al. (Journal of Clinical Pharmacology, 1986; 26, pp. 419-424), (Year: 1986).*
Browne et al. (Journal of Clinical Pharmacology, 1998, 38, pp. 213-220), (Year: 1998).*
Tonn et al. (Biological Mass Spectrometry, 1993, vol. 22 Issue 11, pp. 633-642) (Year: 1993).*
Gupta (Journal of Tropical Pediatrics, vol. 58, No. 5, 2012). (Year: 2012).*
Copenheaver, Blaine R., International Search Report and Written Opinion of the International Searching Authority, PCT/US2020/044204, Dec. 9, 2020.
Tang, Xiaofan, International Preliminary Report on Patentability and Written Opinion, The International Bureau of WIPO, PCT/US2020/044204, Feb. 10, 2022.
Foster, Allan, "Deuterium Isotope Effects in Studies of Drug Metabolism," Trends in Pharmacol. Sci., 5:524-527, 1984.

* cited by examiner

*Primary Examiner* — Umamaheswari Ramachandran

(74) *Attorney, Agent, or Firm* — Gavrilovich, Dodd & Lindsey LLP

(57) ABSTRACT

The disclosure provides for methods and compositions for treating respiratory obstructive diseases.

19 Claims, 12 Drawing Sheets

METHODS AND COMPOSITION FOR TREATING RESPIRATORY OBSTRUCTIVE DISEASES

CROSS REFERENCE TO RELATED APPLICATIONS

This application is a U.S. National Phase Application filed under 35 U.S.C. § 371, and claims the benefit of International Application No. PCT/US2020/044204 filed Jul. 30, 2020, which application claims priority of U.S. Provisional Application No. 62/880,620, filed Jul. 30, 2019, the disclosures of which are incorporated herein by reference in their entirety.

FIELD OF THE INVENTION

Disclosed herein are methods and compositions for treating respiratory obstructive diseases.

BACKGROUND

Abnormal mucus accumulation in airways has deleterious, and fatal consequence in patients suffering from respiratory obstructive diseases, such as cystic fibrosis (CF), chronic obstructive pulmonary disease (COPD) and Asthma. Cystic fibrosis (CF) is a common lethal genetic disease. Approximately one in 3,500 children in the US is born with CF each year. Cystic Fibrosis affects all racial and ethnic groups. An estimated 30,000 American adults and children have CF, and the median predicted age of survival is 37.4 years (CFF Registry Report 2007, Cystic Fibrosis Foundation, Bethesda, Md.). CF is an autosomal recessive hereditary disease caused by a mutation in the gene for the cystic fibrosis transmembrane regulator (CFTR) protein. CF is diagnosed by the level of chloride in sweat because patients with CF have elevated sweat chloride due to the primary defect in CFTR.

Cysteamine is an amino thiol with the chemical formula $HSCH_2CH_2NH_2$. Endogenously, cysteamine is derived from coenzyme A degradation, although its plasma concentrations are low. Cysteamine is commonly used as a drug in the treatment of the orphan disease cystinosis, where it is used to decrease intralysosomal cystine accumulation. However, over the years, cysteamine has been used for several other applications both in vitro and in vivo. Cystamine is an organic disulfide that is the oxidized and dimeric form of cysteamine. Cysteamine is available for clinical use only in the bitartrate salt form (MW 217) and is marketed as prolonged-release (Procysbi™) and an immediate release (Cystagon™) form.

SUMMARY

Abnormal mucus accumulation in airways has deleterious, and fatal consequence in patients suffering from respiratory obstructive diseases, such as cystic fibrosis (CF), COPD and asthma. Therefore, there is a need for therapies aimed at decreasing mucus accumulation to facilitate airway mucus clearance. In the studies presented herein, it was shown that cysteamine-based compounds (e.g., cysteamine, Compound 646, and Compound 656) and cystamine-based compounds (cystamine, Compound 647, and Compound 655) prevented accumulation of viscous mucus and improves mucociliary clearance in ex vivo porcine airway models. Further in vitro studies demonstrate that the compounds of the disclosure reduce native mucin levels, in particular Muc5ac levels, in a dose and time dependent manner. As such, the disclosure demonstrates a correlation between the in vitro and ex vivo results with porcine lung airways and the use of said compounds in treating obstructive respiratory diseases in subjects, including human subjects.

The disclosure provides a method for the treatment of a respiratory obstructive disease in a subject in need thereof, comprising administering to the subject a pharmaceutically acceptable composition comprising an effective amount of a compound having the structure of Formula II:

Formula II

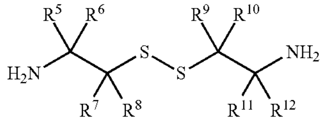

or a pharmaceutically acceptable salt, solvate, or prodrug thereof, wherein $R^5$-$R^{12}$ are independently selected from H or D. In another embodiment, at least one of $R^5$-$R^{12}$ is D. In still another or further embodiment, the compound having a structure of Formula II is selected from:

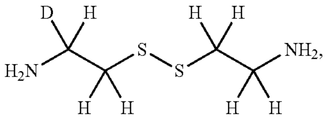,

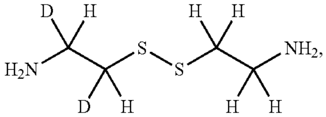,

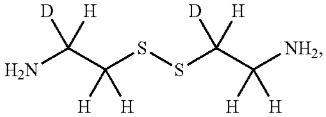,

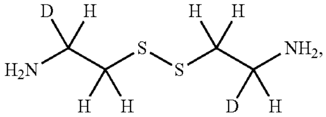,

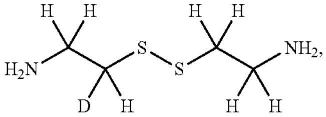,

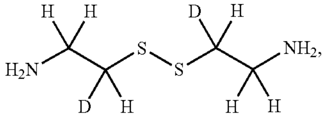,

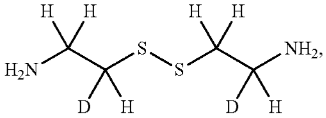,

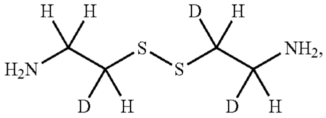,

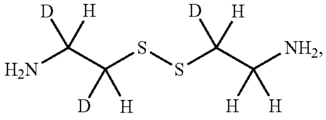,

-continued
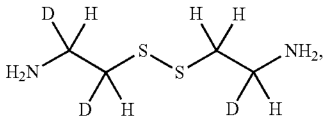
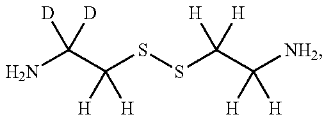
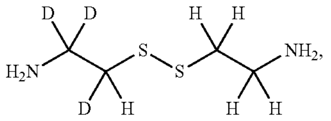
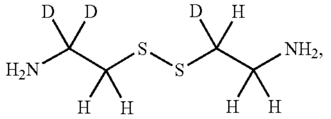
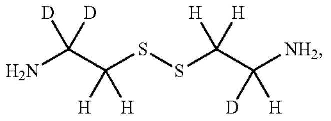
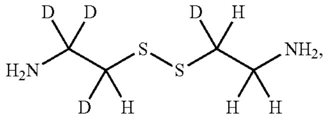
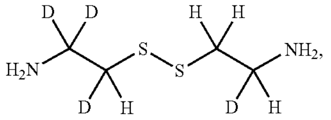
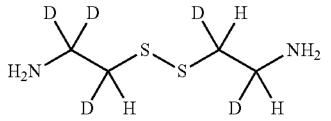
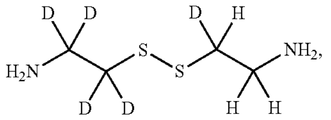
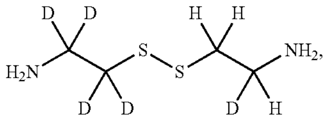
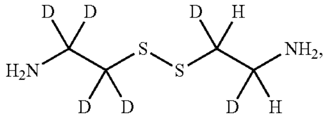
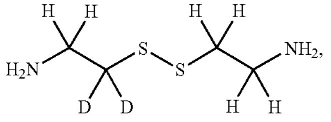
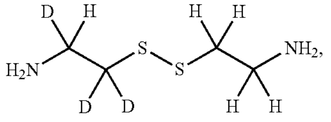
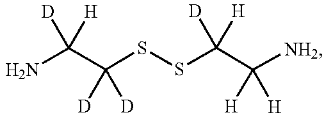
-continued
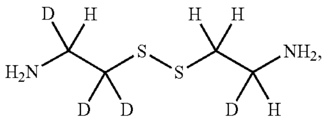
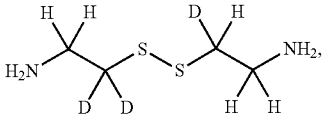
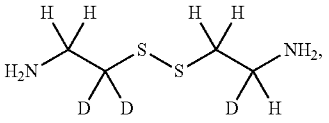
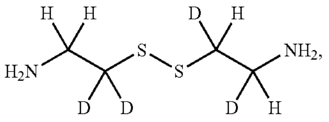
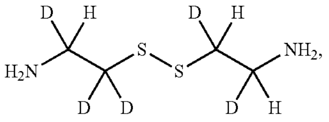
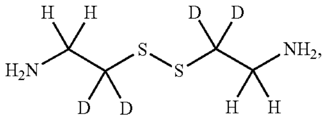
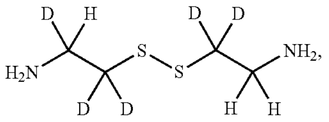
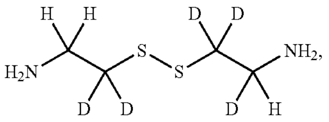
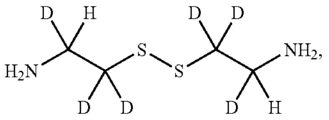
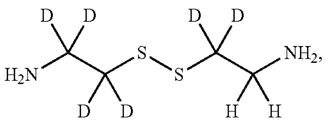
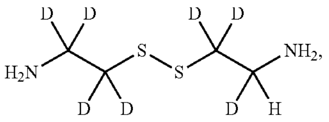
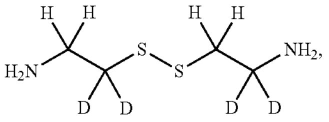
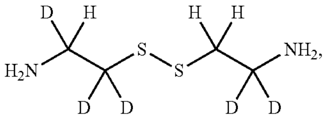
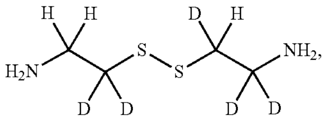

-continued

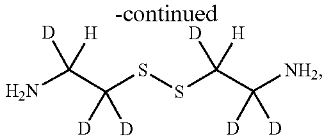

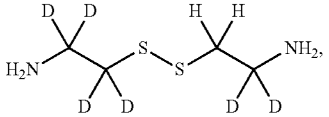

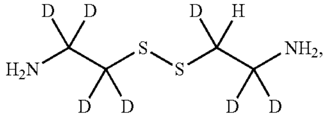

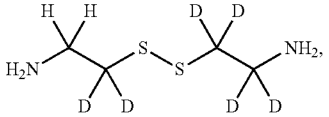

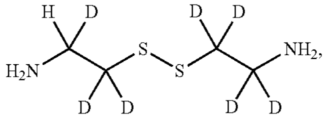

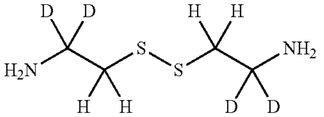

and

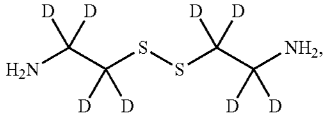

or a pharmaceutically acceptable salt, solvate, or prodrug thereof. In yet another or further embodiment, the compound having a structure of Formula II is selected from:

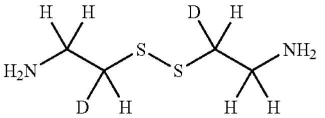

or

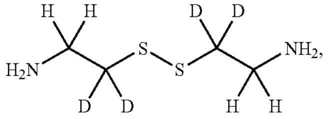

or a pharmaceutically acceptable salt, solvate, or prodrug thereof. In another or further embodiment, the pharmaceutically acceptable composition is formulated for administration by inhalation. In a further embodiment, the pharmaceutically acceptable composition is formulated for administration by a nebulizer. In yet another embodiment the pharmaceutically acceptable composition has a pH from 7 to 9. In yet another or further embodiment, the method further comprises administering by inhalation a second pharmaceutically acceptable composition that has a pH from 4.5 to 6.8, wherein the second pharmaceutically acceptable composition is administered within a short period time after the administration of the first pharmaceutically acceptable composition comprising the compound of Formula II. In a further embodiment, the second pharmaceutically acceptable composition is hyperosmolar 3% saline. In still another or further embodiment, the second pharmaceutically acceptable composition is formulated for administration by a nebulizer. In another or further embodiment, the method further comprises administering a third pharmaceutically acceptable composition comprising a compound having the structure of Formula I or Formula II:

Formula I

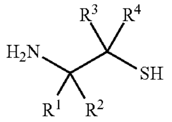

or

Formula II

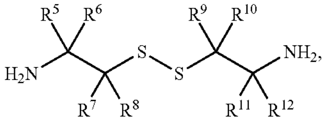

or a pharmaceutically acceptable salt, solvate or prodrug thereof, wherein $R^1$-$R^{12}$ are independently selected from H or D. In a further embodiment, at least one of $R^1$-$R^4$ is D, or wherein at least one of $R^5$-$R^{12}$ is D. In still another or further embodiment, the compound having the structure of Formula I or Formula II is selected from the group consisting of:

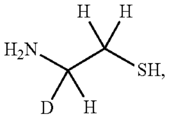

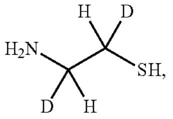

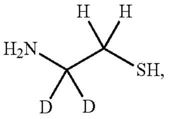

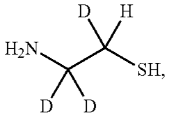

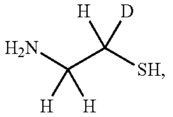

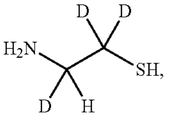

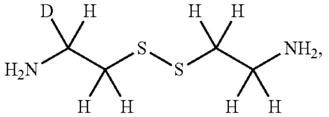

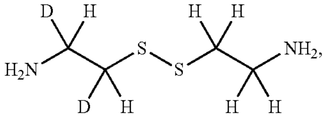

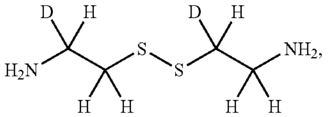

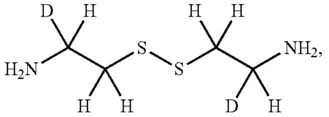

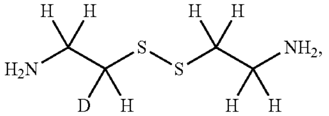

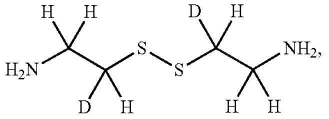

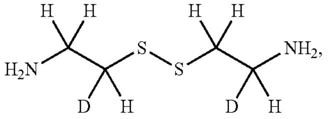

-continued
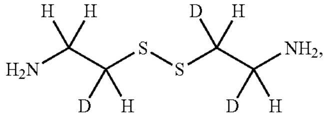,
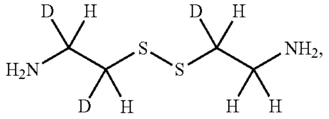,
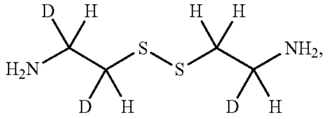,
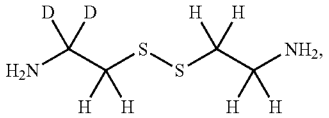,
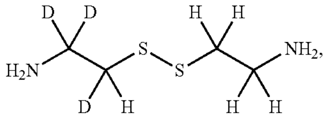,
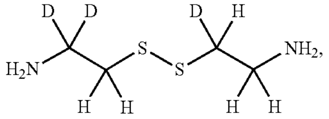,
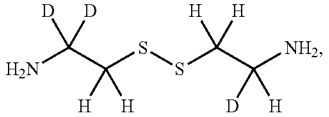,
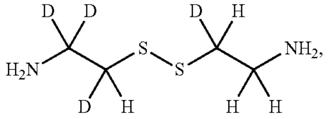,
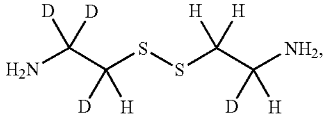,
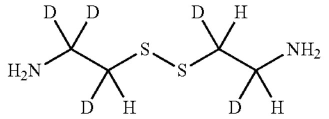
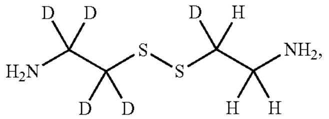,
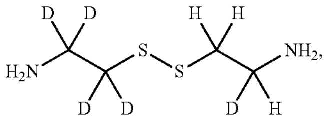,
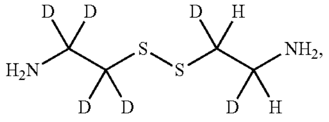,
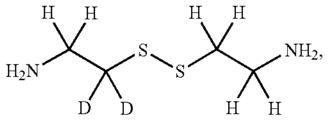,
-continued
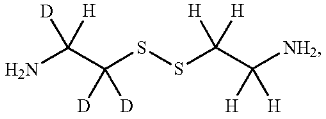,
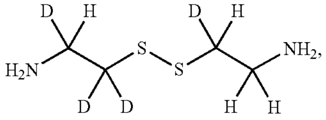,
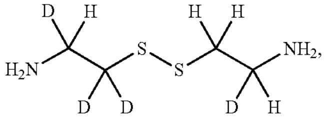,
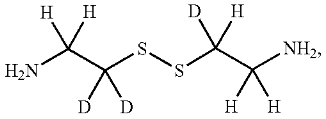,
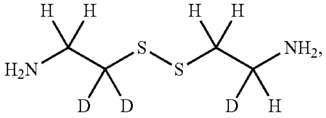,
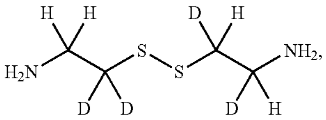,
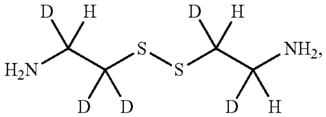,
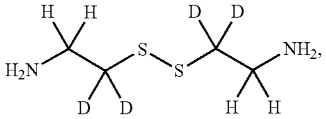,
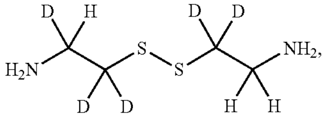,
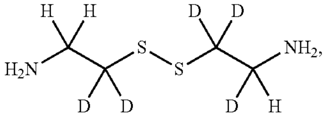,
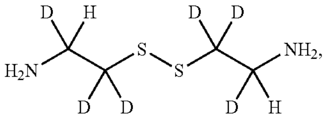,
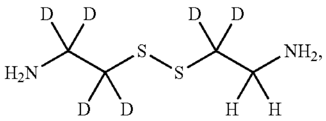,
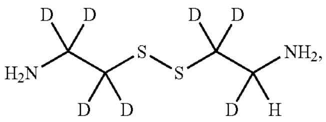,
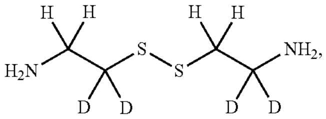, -continued

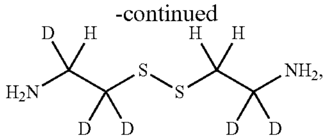

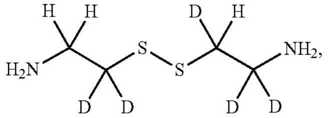

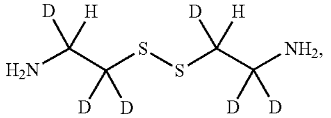

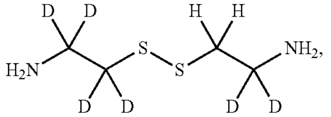

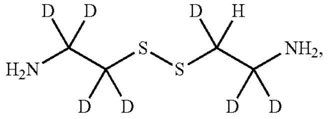

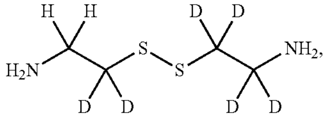

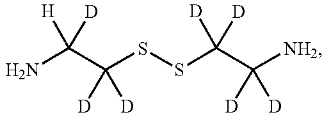

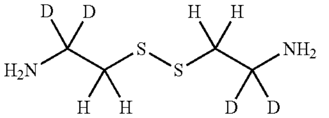

and

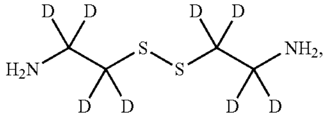

or a pharmaceutically acceptable salt, solvate, or prodrug thereof. In another or further embodiment, the compound is a pharmaceutically acceptable bitartrate salt form of the compound. In another or further embodiment, the third pharmaceutically acceptable composition is formulated for oral delivery. In a further embodiment, the third pharmaceutically acceptable composition is the in the form of granules, tablet, capsule, or caplet. In still another embodiment, the third pharmaceutically acceptable composition is formulated for delayed release. In another or further embodiment, the third pharmaceutically acceptable composition comprises an enteric coating. In yet another or further embodiment, the third pharmaceutically acceptable composition comprises colloidal silicon dioxide, croscarmellose sodium, D&C yellow no. 10 aluminum lake, FD&C blue no. 1 aluminum lake, FD&C blue no. 2 aluminum lake, FD&C red no. 40 aluminum lake, gelatin, magnesium stearate, microcrystalline cellulose, pharmaceutical glaze, pregelatinized starch, silicon dioxide, sodium lauryl sulfate, synthetic black iron oxide and/or titanium dioxide. In yet still further embodiments, the third pharmaceutically acceptable composition comprises microcrystalline cellulose, Eudragit® L 30 D-55, Hypromellose, talc, triethyl citrate, sodium lauryl sulfate, purified water, gelatin, titanium dioxide, blue ink and/or white ink. In yet another embodiment of any of the foregoing, the respiratory obstructive disease is selected from cystic fibrosis, chronic obstructive pulmonary disease, and asthma. In still further embodiments of any of the forgoing, the respiratory obstructive disease is cystic fibrosis. In yet other embodiments, the method is used in combination with one or more agents, devices, and/or techniques useful in the treatment of obstructive respiratory diseases. In further embodiments, one or more techniques and devices useful in the treatment of obstructive respiratory diseases is selected from chest physical therapy, airway clearance techniques, vibrating vest, and/or oxygen therapy. In yet another embodiment, one or more agents useful in the treatment of obstructive respiratory diseases is selected from mucolytic agents, antibiotics, anti-inflammatory medications, bronchodilators, and CFTR Modulator therapies. In a further embodiment, the mucolytic agents are selected from acetylcysteine, ambroxol, bromhexine, carbocisteine, erdosteine, mecysteine, and/or dornase alfa. In yet another embodiment, the CFTR Modulator therapies are selected from ivacaftor, tezacaftor, and/or lumacaftor. In still yet another embodiment, the bronchodilators are selected from albuterol, levalbuterol, ipratropium, aclidinium, arformoterol, formterol, indacaterol, salmeterol, and/or tiotropium. In yet another embodiment, the anti-inflammatory medications are selected from budesonide, fluticasone, beclomethasone, ciclesonide, flunisolide, mometasone, and/or triamcinolone. In a further embodiment of any of the foregoing, the composition of Formula II is administered by inhalation in combination, simultaneously or sequentially with systemic administration or oral administration of a compound of formula I or II. In a further embodiment, following inhalation administration of a compound of formula II, bicarbonate is administered by inhalation to activate or further activate the biological effect of the compound of formula II.

The disclosure also provides a nebulizer or inhaler comprising a compound of Formula II:

Formula II

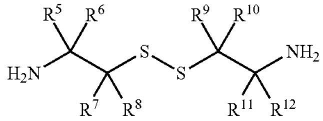

or a pharmaceutically acceptable salt, solvate, or prodrug thereof, wherein $R^5$-$R^{12}$ are independently selected from H or D. In a further embodiment, at least one of $R^5$-$R^{12}$ is D. In still another or further embodiment, the compound having a structure of Formula II is selected from:

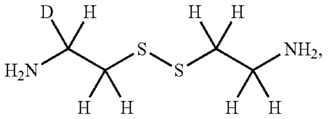

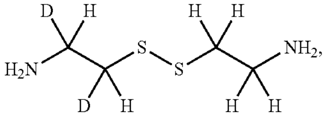

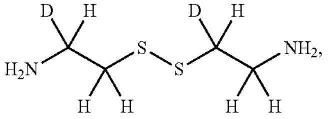

-continued
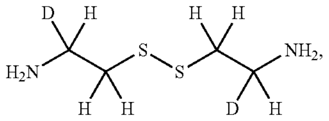,
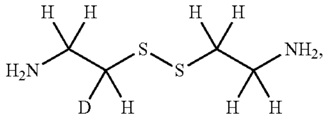,
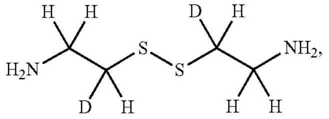,
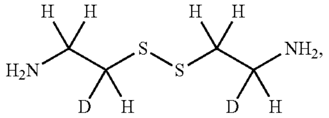,
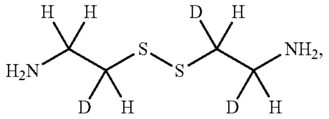,
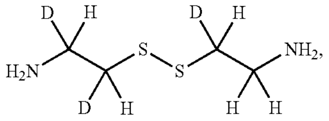,
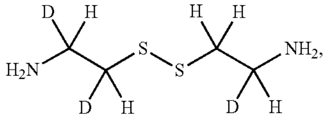,
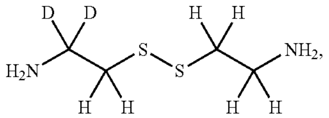,
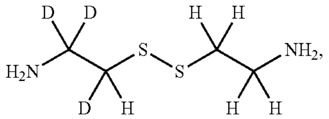,
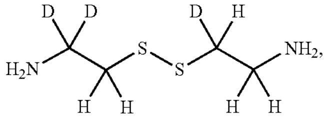,
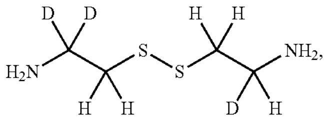,
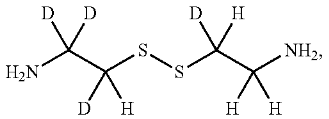,
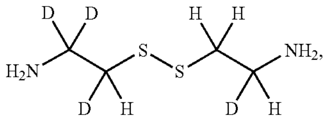,
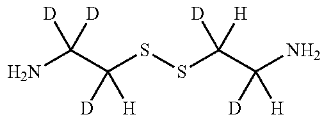
-continued
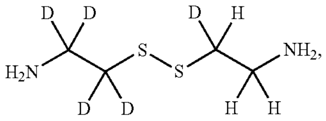,
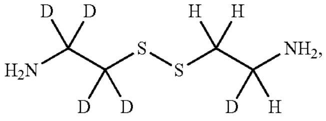,
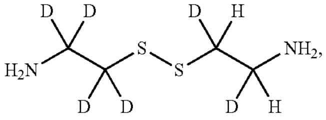,
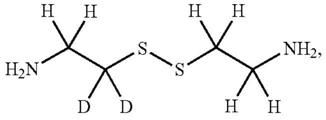,
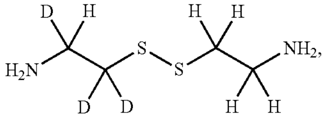,
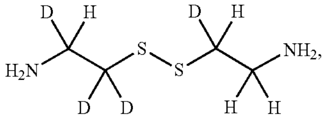,
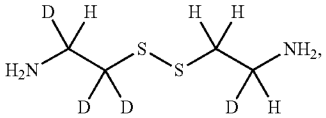,
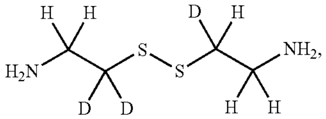,
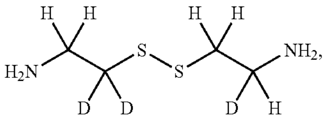,
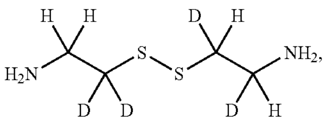,
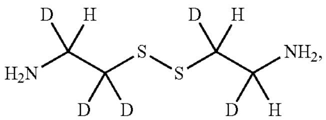,
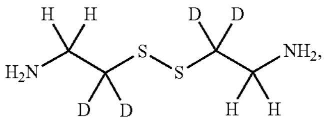,
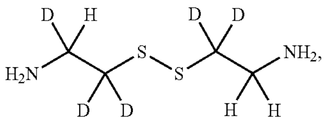,
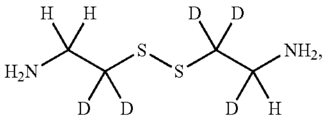, -continued

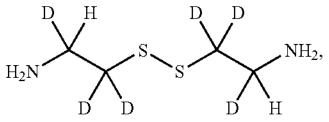,

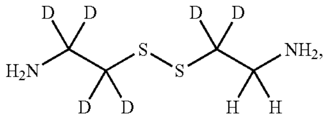,

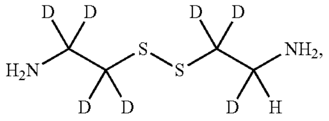,

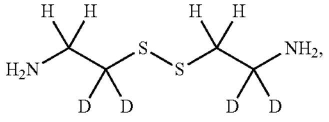,

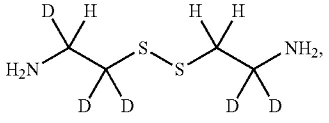,

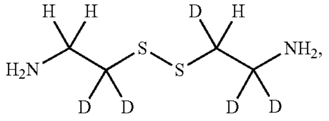,

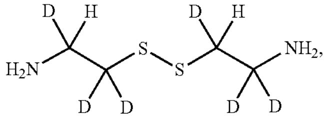,

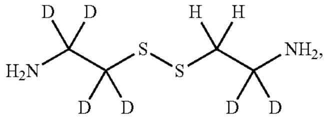,

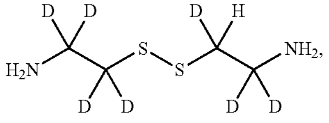,

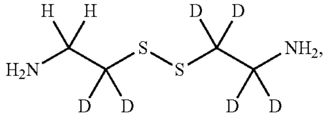,

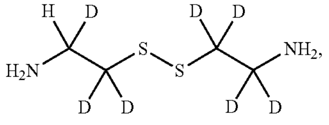,

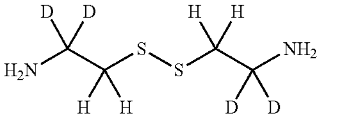 and

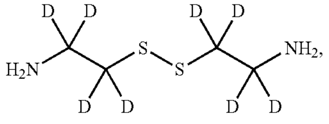, or a pharmaceutically acceptable salt, solvate, or prodrug thereof. In yet another of further embodiment, the compound having a structure of Formula II is selected from:

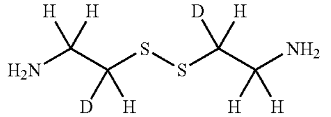 or

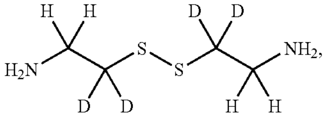, or a pharmaceutically acceptable salt, solvate, or prodrug thereof.

DETAILED DESCRIPTION

Figure 1A:
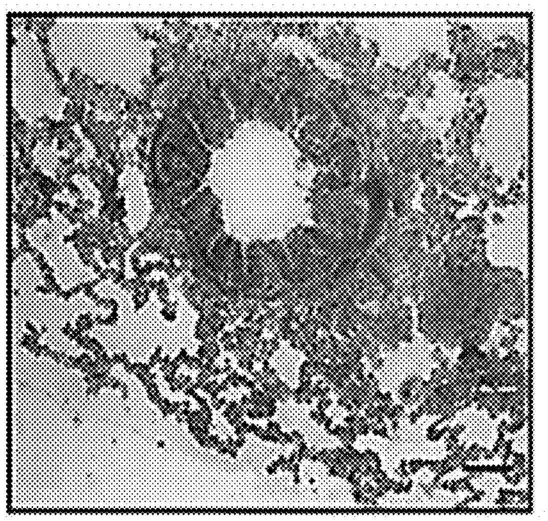
FIG. 1A-D presents photos of airway obstruction caused by cystic fibrosis in human and porcine airways. (A) Shows a normal human airway clean and unobstructed. (B) Periodic acid-Schiff (PAS) staining of human airway shows accumulation of mucin (white arrow) which leads to airway obstruction and death. (C) Shows a normal porcine small airway. (D) PAS staining of porcine small airway shows accumulation of mucin (white arrow) which may lead to airway obstruction and death.
Figure 1B:
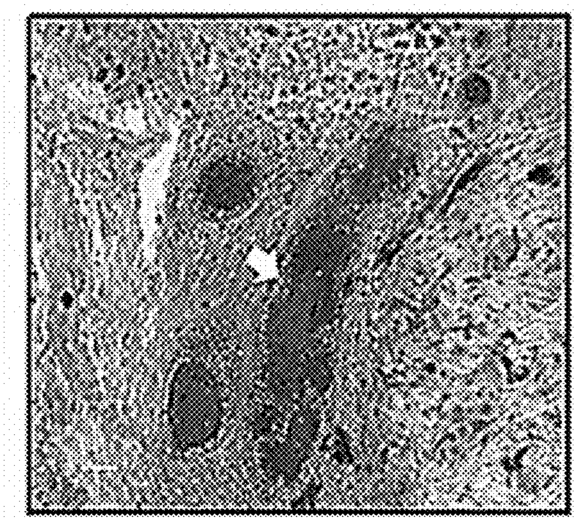
Figure 1C:
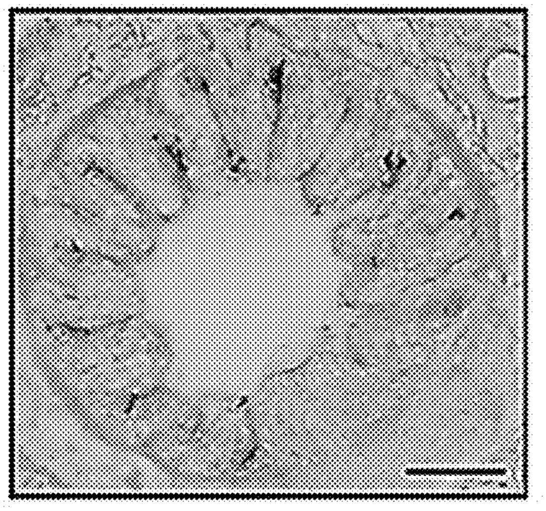
Figure 1D:
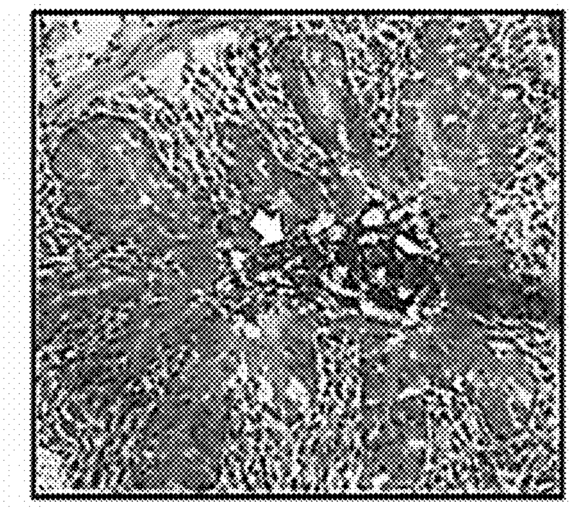
Figure 2:
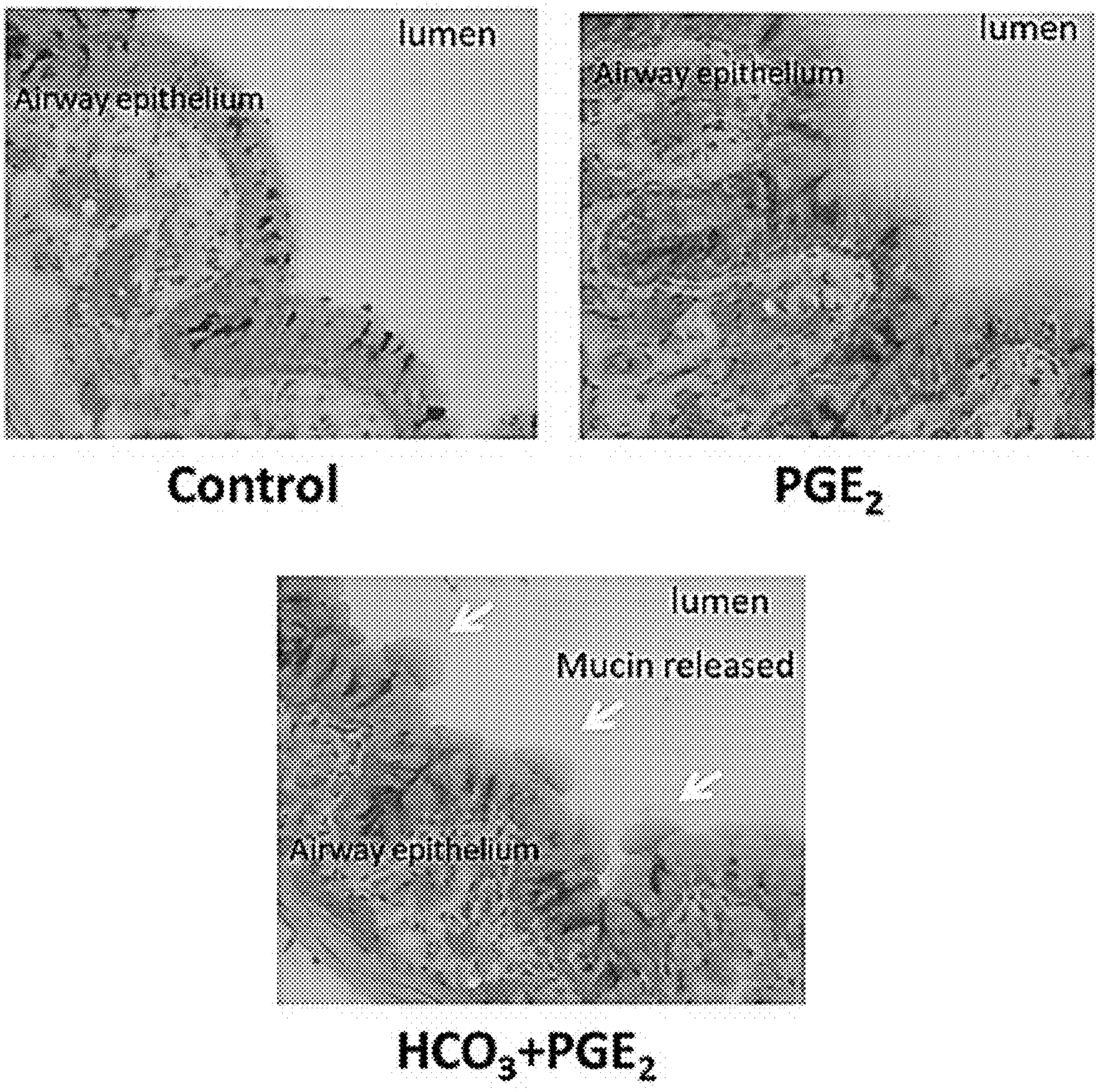
FIG. 2 presents photos demonstrating that bicarbonate and $PGE_2$ increase mucus release in porcine distal epithelium. Freshly isolated distal airways were pre-incubated in equilibrated NaCl-Ringer buffer (Control panel), NaCl-Ringer buffer with $PGE_2$ (1 μM) ($PGE_2$ panel), or in $HCO_3$-Ringer bugger with $PGE_2$ for 15 minutes at 37° C. After incubation, tissues were immediately frozen and maintained at −80° C. for subsequent use in histological processing. Histological sections (5 μM) stained with PAS-Schiff's reagent were analyzed under a microscope. Isolated airways incubated in the presence of bicarbonate and $PGE_2$ showed prominent increase of mucus release over the lining the airway epithelium (white arrows), as compared to the airways incubated with NaCl-Ringer (control) or stimulated with $PGE_2$ in NaCl-Ringer ($PGE_2$). Representative experiment repeated more than four times with similar results.

As used herein and in the appended claims, the singular forms "a," "an" and "the" include plural referents unless the context clearly dictates otherwise. Thus, for example, reference to "a derivative" includes a plurality of such derivatives and reference to "a subject" includes reference to one or more subjects and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The terms "active ingredient", "active compound", and "active Substance" refer to a compound, which is administered, alone or in combination with one or more pharmaceutically acceptable excipients or carriers, to a subject for treating, preventing, or ameliorating one or more symptoms of a disorder.

The term "combination therapy" means the administration of two or more therapeutic agents to treat a disease or disorder described in the present disclosure. Such administration encompasses co-administration of these therapeutic agents in a substantially simultaneous manner, such as in a single capsule having a fixed ratio of active ingredients or in multiple, separate capsules or routes of administration for each active ingredient. In addition, such administration also encompasses use of each type of therapeutic agent in a sequential manner. In either case, the treatment regimen will provide beneficial effects of the drug combination in treating the disorders described herein.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials are about 0.0156%. The deuterium enrichment can be determined using conventional analytical methods known to one of ordinary skill in the art, including mass spectrometry and nuclear magnetic resonance spectroscopy.

The term "is/are deuterium", when used to describe a given position in a molecule such as R-R or the symbol "D." when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and Symptoms.

The terms "drug" and "therapeutic agent" refer to a compound, or a pharmaceutical composition thereof, which is administered to a subject for treating, preventing, or ameliorating one or more symptoms of a disorder.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

The term "non-release controlling excipient" refers to an excipient whose primary function does not include modifying the duration or place of release of the active substance from a dosage form as compared with a conventional immediate release dosage form.

The term "pharmaceutically acceptable carrier, "pharmaceutically acceptable excipient", "physiologically acceptable carrier", or "physiologically acceptable excipient" refers to a pharmaceutically-acceptable material, composition, or vehicle, such as a liquid or Solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, Remington. The Science and Practice of Pharmacy, 21st Edition; Lippincott Williams & Wilkins: Philadelphia, Pa., 2005, Handbook of Pharmaceutical Excipients, 5th Edition; Rowe et al., Eds. The Pharmaceutical Press and the American Pharmaceutical Association: 2005; and Handbook of Pharmaceutical Additives, 3rd Edition; Ash and Ash Eds. Gower Publishing Company: 2007; Pharmaceutical Preformulation and Formulation, Gibson Ed., CRC Press LLC: Boca Raton, Fla., 2004).

The terms "prevent", "preventing", and "prevention" refer to a method of delaying or precluding the onset of a disorder, and/or its attendant symptoms, barring a subject from acquiring a disorder or reducing a subject's risk of acquiring a disorder.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, Progress in Drug Research 1962, 4, 221-294; Morozowich et al. in "Design of Biopharmaceutical Properties through Prodrugs and Analogs. Roche Ed., APHA Acad. Pharm. Sci. 1977: "Bioreversible Carriers in Drug in Drug Design, Theory and Application." Roche Ed., APHA Acad. Pharm. Sci. 1987: "Design of Prodrugs." Bundgaard, Elsevier, 1985; Wang et al., *Curr. Pharm. Design* 1999, 5, 265-287: Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems." Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209: Browne, *Clin. Neuropharmacol.* 1997, 20, 1-12; Bundgaard, *Arch. Pharm. Chem.* 1979, 86, 1-39: Bundgaard, *Controlled Drug Delivery* 1987, 17, 179-96: Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877: Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45,866-94: Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

The term "release controlling excipient" refers to an excipient whose primary function is to modify the duration or place of release of the active substance from a dosage form as compared with a conventional immediate release dosage form.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, Swine (e.g., pig, miniature pig), equine, canine, feline, and the like. The terms "subject' and "patient" are used interchangeably herein in reference, for example, to a mammalian subject, such as a human patient.

The term "substantially" as used herein refers to a majority of, or mostly, as in at least about 51%, 60%, 70%, 80%, 90%, 95%, 96%, 97%, 98%, 99%, 99.5%, 99.9%, 99.99%, or at least about 99.999% or more.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, Veterinarian, medical doctor, or clinician.

The term "therapeutically acceptable" refers to those compounds (or salts, prodrugs, tautomers, Zwitterionic forms, etc.) which are suitable for use in contact with the tissues of patients without excessive toxicity, irritation, allergic response, immunogenicity, are commensurate with a reasonable benefit/risk ratio, and are effective for their intended use.

The terms "treat", "treating", and "treatment" are meant to include alleviating or abrogating a disorder or one or more of the symptoms associated with a disorder; or alleviating or eradicating the cause(s) of the disorder itself. As used herein, reference to "treatment of a disorder" is intended to include prevention.

The compounds disclosed herein can and do exist as therapeutically acceptable salts. The term "pharmaceutically acceptable salt", as used herein, represents salts or Zwitterionic forms of the compounds disclosed herein which are therapeutically acceptable as defined herein. The salts can be prepared during the final isolation and purification of the compounds or separately by reacting the appropriate compound with a suitable acid or base. Therapeutically accept able salts include acid and basic addition salts. For a more complete discussion of the preparation and selection of salts, refer to "Handbook of Pharmaceutical Salts, Properties, and Use." Stah and Wermuth, Ed. (Wiley-VCH and VHCA, Zurich, 2002) and Berge et al., *J. Pharm. Sci.* 1977, 66, 1-19.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-Sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, C—OXO-glutaric acid, glycolic acid, hippuric acid, hydrobromic acid, hydrochloric acid, hydroiodic acid, (+)-L-lactic acid, (t)-DL-lactic acid, lactobionic acid, lauric acid, maleic acid, (−)-L-malic acid, malonic acid, (+)-DL mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

Airway obstruction with thick, adherent mucus is a pathophysiologic and clinical feature of obstructive respiratory diseases, including chronic obstructive pulmonary disease (COPD), asthma and cystic fibrosis (CF). Mucins, the dominant biopolymer in mucus, organize into complex polymeric networks via the formation of covalent disulfide bonds, which govern the viscoelastic properties of the mucus gel. The compounds disclosed herein disrupt native mucin levels (in particular Muc5ac levels) in porcine airway epithelium, most likely via reduction of the disulfide bonds making mucin polymeric networks.

In healthy individuals, mucus is secreted by airway epithelial cells and submucosal glands to trap and clear inhaled particles from the lung. The biophysical properties of airway mucus are governed by the secreted polymeric mucins, MUC5AC and MUC5B, which are high-molecular-weight glycoproteins that organize into large multimers (2-100 MDa) via the formation of inter-molecular disulfide bonds. In obstructive respiratory diseases, including chronic bronchitis (CB), asthma and cystic fibrosis (CF), mucin hypersecretion, hyperconcentration and increased mucin cross-linking slow mucus transport, producing persistent mucus plugging and airflow obstruction.

Cystic fibrosis (CF) is a genetic disorder that affects mostly the lungs, but also the pancreas, liver, kidneys, and intestine. Long-term issues include difficulty breathing and coughing up mucus as a result of frequent lung infections. CF is inherited in an autosomal recessive manner. It is caused by the presence of mutations in both copies of the gene for the cystic fibrosis transmembrane conductance regulator (CFTR) protein. Those with a single working copy are carriers and otherwise mostly normal. CFTR is involved in production of sweat, digestive fluids, and mucus. When the CFTR is not functional, secretions which are usually thin, instead, become thick. The condition is diagnosed by a sweat test and genetic testing. There is no known cure for cystic fibrosis. Lung disease results from clogging of the airways due to mucus build-up, decreased mucociliary clearance, and resulting inflammation. Inflammation and infection cause injury and structural changes to the lungs, leading to a variety of symptoms. Lung infections are treated with antibiotics which may be given intravenously, inhaled, or by mouth. Sometimes, the antibiotic azithromycin is used long term. Inhaled hypertonic saline and salbutamol may also be useful. Lung transplantation may be an option if lung function continues to worsen. Airway clearance techniques such as chest physiotherapy have some short-term benefit, but long-term effects are unclear. The average life expectancy is between 42 and 50 years in the developed world. Lung problems are responsible for death in 80% of people with cystic fibrosis.

Most of the damage in CF is due to blockage of the narrow passages of affected organs with thickened secretions. Recent advances in the treatment of cystic fibrosis have meant that individuals with cystic fibrosis can live a fuller life less encumbered by their condition. The cornerstones of management are the proactive treatment of airway infection, and encouragement of good nutrition and an active lifestyle. Pulmonary rehabilitation as a management of CF continues throughout a person's life, and is aimed at maximizing organ function, and therefore the quality of life. At best, current treatments delay the decline in organ function. Because of the wide variation in disease symptoms, treatment typically occurs at specialist multidisciplinary centers and is tailored to the individual. The most consistent aspect of therapy in CF is limiting and treating the lung damage caused by thick mucus and infection, with the goal of maintaining quality of life. Aerosolized medications that help loosen secretions include dornase alfa and hypertonic saline. Dornase is a recombinant human deoxyribonuclease, which breaks down DNA in the sputum, thus decreasing its viscosity. Denufosol, an investigational drug, opens an alternative chloride channel, helping to liquefy mucus. Ivacaftor is a medication taken by mouth for the treatment of CF due to a number of specific mutations responsive to ivacaftor-induced CFTR protein enhancement. It improves lung function by about 10%; however, as of 2014 it is expensive. The first year it was on the market, the list price was over $300,000 per year in the United States. In July 2015, the U.S. Food and Drug Administration approved lumacaftor/ivacaftor. In 2018, the FDA approved the combination ivacaftor/tezacaftor; the manufacturer announced a list price of $292,000 per year. Tezacaftor helps move the CFTR protein to the correct position on the cell surface, and is designed to treat people with the F508del mutation. Intravenous, inhaled, and oral antibiotics are used to treat chronic and acute infections. It should be noted that any of the above existing compositions can be used in combination with the compositions of the present invention.

Mechanical devices and inhalation medications are used to alter and clear the thickened mucus. One technique is chest physiotherapy where a respiratory therapist percusses an individual's chest by hand several times a day, to loosen up secretions. This "percussive effect" can be administered also through specific devices that device chest wall oscillation or intrapulmonary percussive ventilator. Other methods such as biphasic cuirass ventilation, and associated clearance mode available in such devices, integrate a cough assistance phase, as well as a vibration phase for dislodging secretions. These are portable and adapted for home use. Chest physiotherapy is beneficial for short-term airway clearance. Another technique is positive expiratory pressure physiotherapy that consists of providing a back pressure to the airways during expiration. This effect is provided by devices that consists of a mask or a mouthpiece in which a resistance is applied only on the expiration phase. Operating principles of this technique seems to be the increase of gas pressure behind mucus through collateral ventilation along with a temporary increase in functional residual capacity preventing the early collapse of small airways during exhalation. The compositions of the disclosure can be used in combination with any of the foregoing devices and methods provided above.

As lung disease worsens, mechanical breathing support may become necessary. Individuals with CF may need to wear special masks at night to help push air into their lungs. These machines, known as bilevel positive airway pressure (BiPAP) ventilators, help prevent low blood oxygen levels during sleep. Non-invasive ventilators may be used during physical therapy to improve sputum clearance. It is not known if this type of therapy has an impact on pulmonary exacerbations or disease progression. It is not known what role non-invasive ventilation therapy has for improving exercise capacity in people with cystic fibrosis. During severe illness, a tube may be placed in the throat (a procedure known as a tracheostomy) to enable breathing supported by a ventilator. Oxygen therapy at home is recommended in those with significant low oxygen levels.

Detailed examination of CFTR expression in organs and different cell types indicates that changes in CFTR expression do not always correlate with the severity of CF disease or mucus accumulation. Thus, the mucus hyperproduction that typifies CF does not appear to be a direct cause of a defective CFTR but, rather, to be a downstream consequence. In organs like the lung, up-regulation of mucin gene expression by inflammation results from chronic infection; however, in other instances and organs, the inflammation may have a non-infectious origin. The mucus plugging phenotype of the β-subunit of the epithelial $Na^+$ channel ($\beta ENaC)^-$overexpressing mouse is proving to be an archetypal example of this kind of inflammation, with a dehydrated airway surface/concentrated mucus gel apparently providing the inflammatory stimulus. Data indicate that the luminal $HCO_3^-$ deficiency recently described for CF epithelia may also provide such a stimulus, perhaps by causing a mal-maturation of mucins as they are released onto luminal surfaces. Mucins are high molecular weight glycoproteins bearing cysteine-rich domains able to form intramolecular disulfide bonds. Mucins are also overexpressed in lung diseases such as asthma, bronchitis, chronic obstructive pulmonary disease (COPD) or cystic fibrosis.

For decades, mucolytic agents have been pursued as a therapeutic approach to treat obstructive respiratory diseases. Reducing agents that disrupt the mucin inter-molecular covalent disulfide bonds are predicted to de-adhere mucus from airway surfaces and improve clearance. Mucomyst® (N-acetylcysteine or NAC) was approved as an inhaled therapy for patients with CF and CB in the 1960s. However, clinical data in CF and COPD do not support the efficacy of inhaled NAC with respect to improvement of lung function or reduction in pulmonary exacerbations. These negative clinical NAC studies have limited the enthusiasm for inhaled mucolytics as therapeutic options for muco-obstructive lung diseases. In contrast, recombinant human DNase (rhDNase or Dornase alfa), an enzyme that breaks down the extracellular DNA released by dying neutrophils entrapped in the mucus, produced substantial clinical benefits in adult CF subjects. These positive results validated the concept that an inhaled drug that affects the rheology of airway secretions could improve health outcomes. However, rhDNase is only active in CF subjects with persistent inflammation and was ineffective in obstructive diseases other than CF. Recently, reducing agents have been reported to produce greater effects on CF sputum viscoelasticity than rhDNase in vitro, suggesting they may benefit CF subjects and a broader population.

In pulmonary medicine, there has been a long-standing need to treat diseases associated with mucus accumulation in the lungs. The overarching goal of an inhaled therapy is to clear the hyperconcentrated, adherent mucus that causes airflow obstruction, inflammation, and infection.

Cysteamine is a sulfhydryl reducing agent able to disrupt both intramolecular and intermolecular disulfide bonds. Cysteamine is an approved medical drug in cystinosis, which has shown mucolytic activity, bactericidal and anti-biofilm properties. Cysteamine markedly reduces intralysosomal cysteine accumulation in cystinosis. Cysteamine can increase the cellular thiol and free thiol tripeptide glutathione pool, and thus modulate reactive oxygen species (ROS) scavenging, and decreased lipoperoxidation and glutathione peroxidase activity. Furthermore, cysteamine also increases adiponectin levels.

Cystamine, in addition to its role as a radioprotectant, has been found to alleviate tremors and prolong life in mice with the gene mutation for Huntington's disease (HD). The drug may work by increasing the activity of proteins that protect nerve cells, or neurons, from degeneration. Cystamine appears to inactivate an enzyme called transglutaminase and thus results in a reduction of huntingtin protein. In addition, cystamine was found to increase the levels of certain neuroprotective proteins. However, due to the current methods and formulation of delivery of cystamine, degradation and poor uptake require excessive dosing.

Deuteration of pharmaceuticals to improve pharmacokinetics (PK), pharmacodynamics (PD), and toxicity profiles has been demonstrated previously with some classes of drugs. For example, the deuterium kinetic isotope effect (DKIE) was used to decrease the hepatotoxicity of halothane, presumably by limiting the production of reactive species such as trifluoroacetylchloride. However, this method may not be applicable to all drug classes. For example, deuterium incorporation can lead to Metabolic Switching. Metabolic Switching occurs when xenogens, sequestered by Phase I enzymes, bind transiently and re-bind in a variety of conformations prior to the chemical reaction (e.g., oxidation). Metabolic switching is enabled by the relatively vast size of binding pockets in many Phase I enzymes and the promiscuous nature of many metabolic reactions. Metabolic switching can lead to different proportions of known metabolites as well as altogether new metabolites. This new metabolic profile may impart more or less toxicity. Such pitfalls are non-obvious and are not predictable a priori for any drug class.

Cysteamine is a small aminothiol molecule that is easily transported across cellular membranes. Cystamine is a small disulfide molecule that can be reduced into 2× cysteamine molecules. The carbon-hydrogen bonds of cysteamine and cystamine contain a naturally occurring distribution of hydrogen isotopes, namely H or protium (about 99.984.4%), H or deuterium (about 0.0156%), and H or tritium (in the range between about 0.5 and 67 tritium atoms per 10' protium atoms). Increased levels of deuterium incorporation produces a detectable Kinetic Isotope Effect (KIE) that affects the pharmacokinetic, pharmacologic and/or toxicologic profiles.

Cysteamine is metabolized in vivo by first being converted to hypotaurine by the action of the cysteamine dioxygenase. Hypotaurine is then oxidized to taurine by the action of hypotaurine dehydrogenase. Cystamine is reduced in vivo into cysteamine and RS-cysteamine mixed disulfide by thiol-disulfide exchange. Cysteamine is then metabolized as above. The current approach has the potential to prevent or retard metabolism at these sites, such as retarding the conversion of cysteamine to hypotaurine. Other sites on the molecule may also undergo transformations leading to metabolites with as-yet unknown pharmacology/toxicology. Limiting the production of such metabolites has the potential to decrease the danger of the administration of such drugs and may even allow increased dosage and concomitant increased efficacy. All of these transformations, among other potential transformations, can occur through polymorphically-expressed enzymes, leading to interpatient variability. Further, it is quite typical for disorders, such as cystic fibrosis, to produce symptoms that are best medicated around the clock for extended periods of time. The compounds of the disclosure can provide for long term effects compared to non-deuterated forms of the compound.

Figure 3:
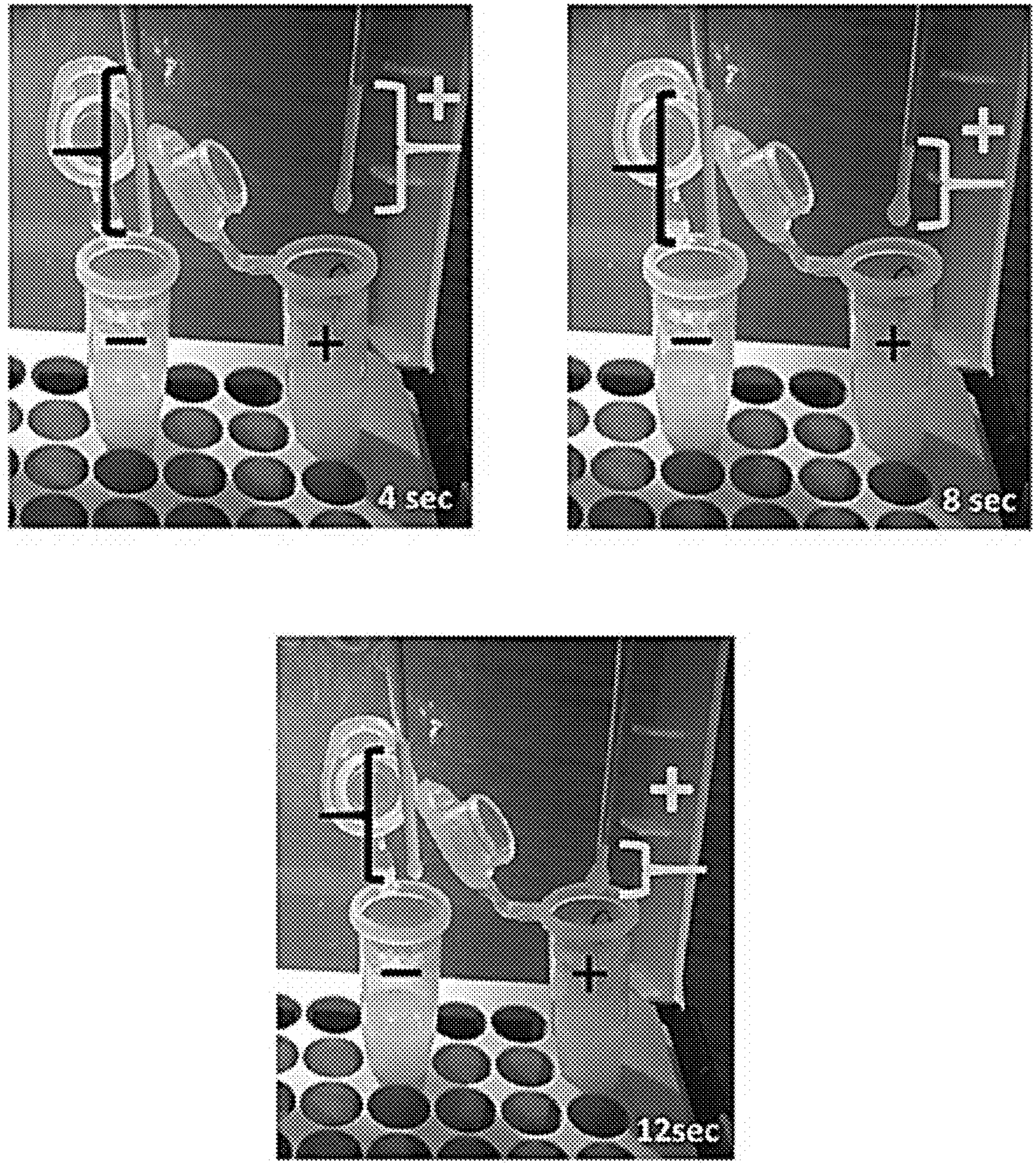
FIG. 3 demonstrates the mucolytic activity of cysteamine bitartrate. Porcine mucin 15% (W/V) was incubated in Ringer buffer solution containing bicarbonate (25 mM) in the presence (+) or absence (−) of Cysteamine bitartrate (10 mg/mL), for 4 h at 37° C. Thereafter, equal volume of mucin solution from each condition were aspirated separately in a sterile Pasteur pipette. Changes in mucin viscosity was measured by the rapidity of the volume displaced toward the bottom of the pipette, as indicated in each panel (0-12 seconds). Mucin solution containing cysteamine (+) showed an increase in solubility, as compared with the mucin solution without cysteamine.
Figure 4:
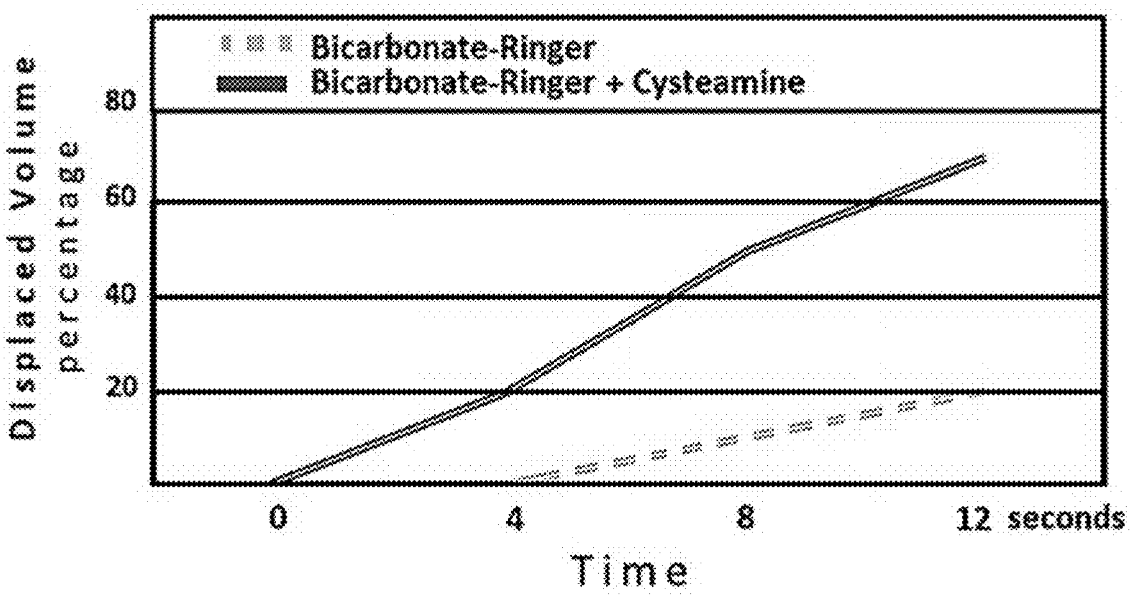
FIG. 4 demonstrates the mucolytic activity of cysteamine bitartrate in Ringer buffer solution containing bicarbonate. Porcine mucin 15% (W/V) was incubated in Ringer buffer solution containing bicarbonate (25 mM) in the presence (+) or absence (−) of cysteamine bitartrate (10 mg/mL), for 4 hours at 37° C. Changes in mucin viscosity was determined by the percentage of volume displaced as a function of time (0-12 seconds) through a vertical sterile Pasteur pipette tip at room temperature. The graph shows the changes in mucin viscosity observed in the mucin solutions containing the presence of cysteamine (black line), as compared with the mucin solution without cysteamine (blue line).
Figure 5:
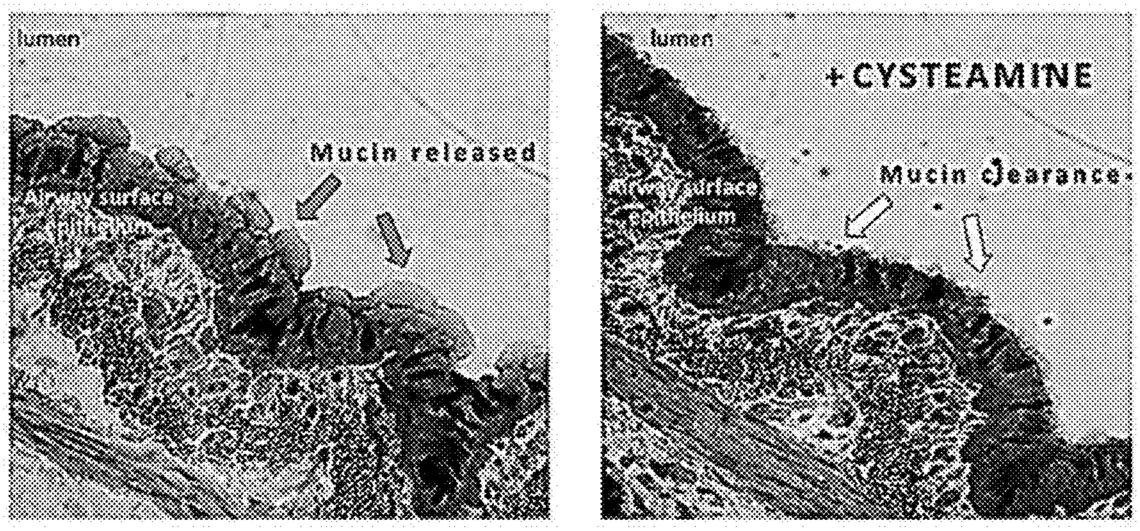
FIG. 5 demonstrates that cysteamine bitartrate facilitates mucin clearance on surface airway epithelium. Cysteamine facilitates clearance of mucin released over the luminal airway surface. Porcine airways were incubated in the presence of buffer containing bicarbonate (25 mM) and $PGE_2$ (10 μM) for 5 min at 37° C. Thereafter, airways were subsequently incubated in the presence or absence of Cysteamine (200 μM) for an additional 5 min. Airways, were harvested and processed for histological analysis. Mucin released over the airway surface epithelium was cleared from the luminal surface in airways containing cysteamine. Suggesting that cysteamine can have beneficial impact in mucociliary clearance in patient suffering from cystic fibrosis and chronic obstructive pulmonary disease.
Figure 6:
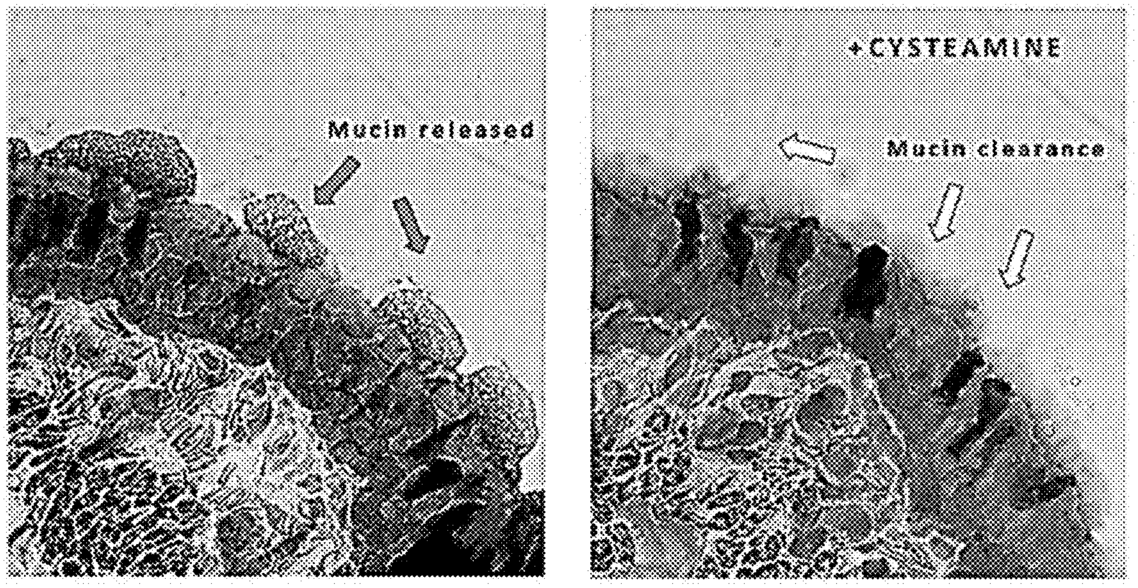
FIG. 6 provides for close up images of the photos presented in FIG. 5.

As is shown in the experiments presented herein, cysteamine decreased mucus accumulation and improve mucociliary clearance under normal and cystic fibrosis physiological conditions in isolated native airways. In particular, a notable decrease in porcine mucin viscosity resulted when cysteamine bitartrate was added to a Ringer buffer solution comprising bicarbonate than use of said solution lacking cysteamine bitartrate (e.g., see FIG. 3). Further as shown in FIG. 4, the displaced volume percentage of porcine mucin was noticeably reduced in the sample comprising cysteamine/bicarbonate vs. without, and further exhibited a more consistent displaced volume percentage over time than samples that lacked cysteamine bitartrate. Additionally, studies looking at the effect of cysteamine bitartrate on mucin clearance on luminal airway surfaces clearly shows that compositions which comprise cysteamine has a beneficial effect on mucin clearance on airway surface epithelium (e.g., see FIG. 5 and FIG. 6). Accordingly, the foregoing studies indicate that cysteamine can make a beneficial impact in mucociliary clearance in patient suffering from a respiratory obstructive disease.

Figure 7:
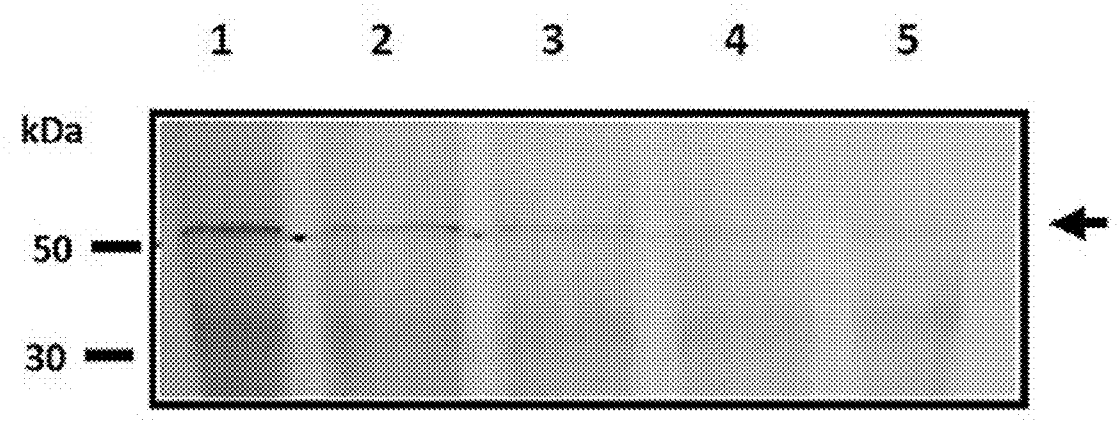
FIG. 7 presents the effects of cysteamine bitartrate and compound 646 on porcine gastric mucin extract. One hundred microliters of gastric mucin extract (5 mg/mL) was incubated with and without cysteamine bitartrate and compound 646 separately, at 37° C. for 60 minutes. Electrophoresis analysis of untreated gastric mucin extract showed two major protein bands visualized after staining, at the level of 50 kDa and 30 kDa (lane 1). Gastric mucin extract treated with Cysteamine bitartrate at 200 μM (lane 2) and 400 μM (lane 3), showed a reduction of the 50 kDa protein band. In samples treated with compound 646 at 200 μM (lane 4) and 400 μM (lane 5) showed also a decrease in the 50 kDa protein band.
Figure 8:
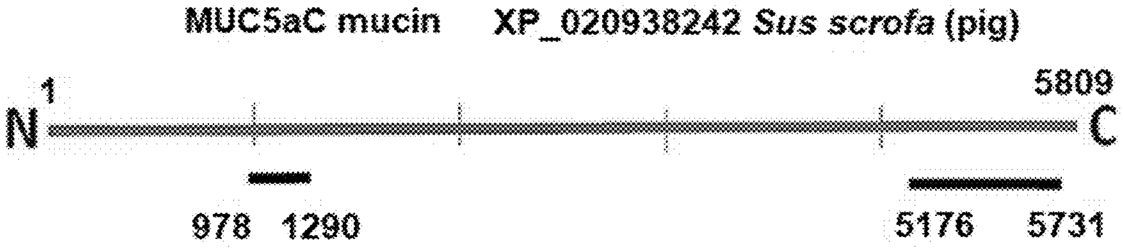
FIG. 8 provides mass spectrometry analysis of the 50 kDa protein band from gastric mucin extract. The 50 kDa protein band visible after electrophoresis protein separation of gastric mucin extract was carefully cut from the gel and analyzed by mass spectrometry. Seventeen peptides were identified to match amino acid sequences found on porcine Muc5aC mucin. The identified peptides were located around two protein regions of Muc5ac mucin from 978-1290, and from 5176-5731 amino acids sequence.
Figure 10:
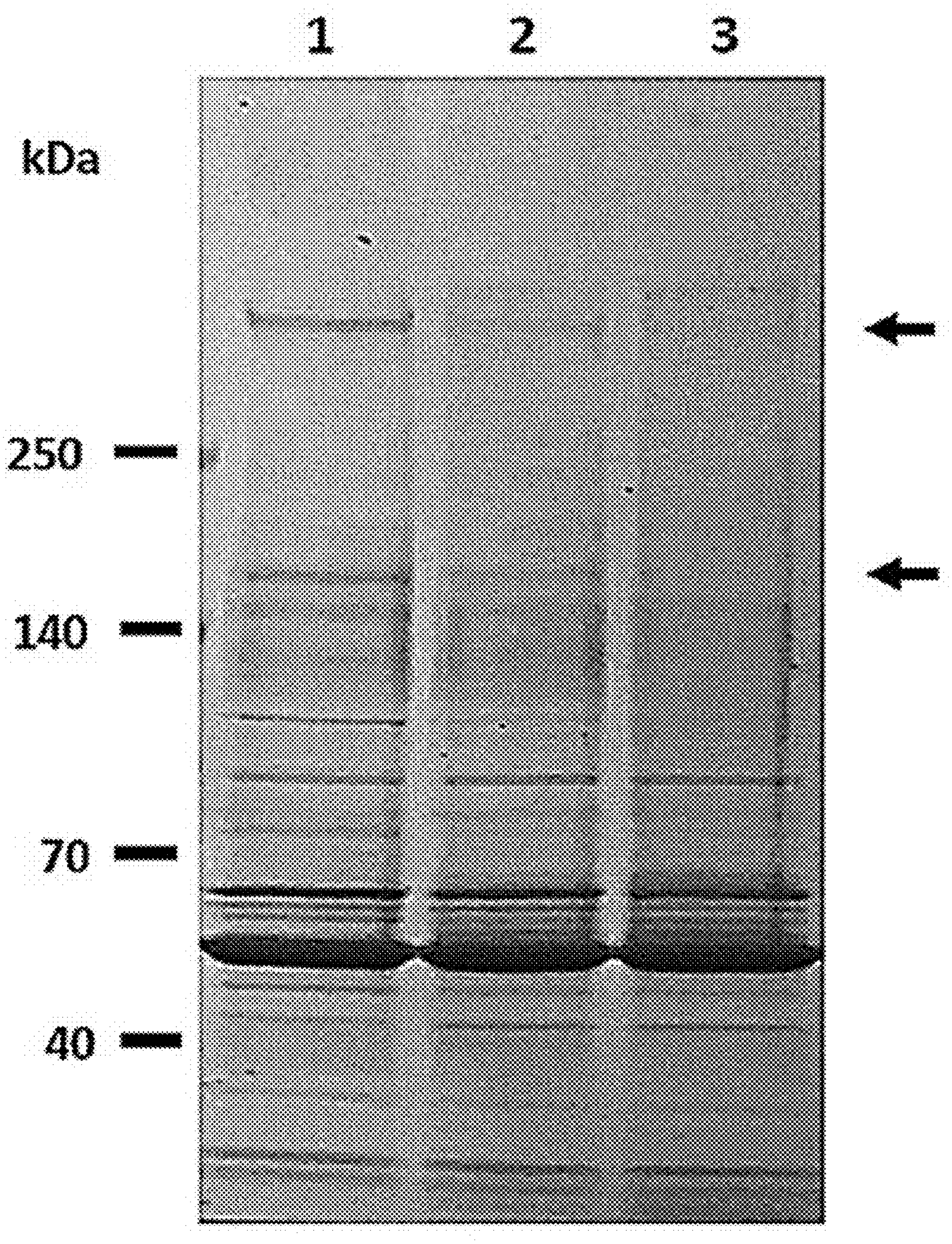
FIG. 10 demonstrates the effect of cysteamine bitartrate on airway mucus under basic and acidic conditions. Airway mucus supernatant diluted in $NaHCO_3$-Ringer was treated with or without cysteamine bitartrate under basic and acidic conditions at 37° C. for 60 minutes. Lane 1 shows a representative protein pattern after electrophoresis protein separation of untreated porcine airway mucus supernatant diluted in $NaHCO_3$-Ringer solution (40 μg/well). In lane 2 electrophoretic separation of airway mucus treated with 2 mM cysteamine bitartrate (diluted in $NaHCO_3$-Ringer pH 8), which showed a minor decrease in the proteins visualized at the level of 600 and 200 kDa. In contrast (lane 3), airway mucus treated with 2 mM cysteamine bitartrate, and supplemented with 4 μL of 0.1 N acetic solution (pH 4.5) showed a significant reduction in the protein bands visualized at 600 and 200 kDa (black arrows).
Figure 11:
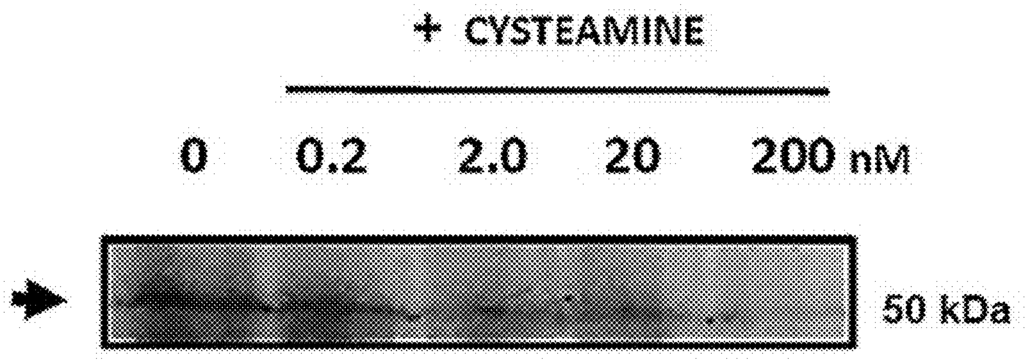
FIG. 11 showing the effects of cysteamine at nM concentrations, on mucin extracted from porcine guts.
Figure 12:
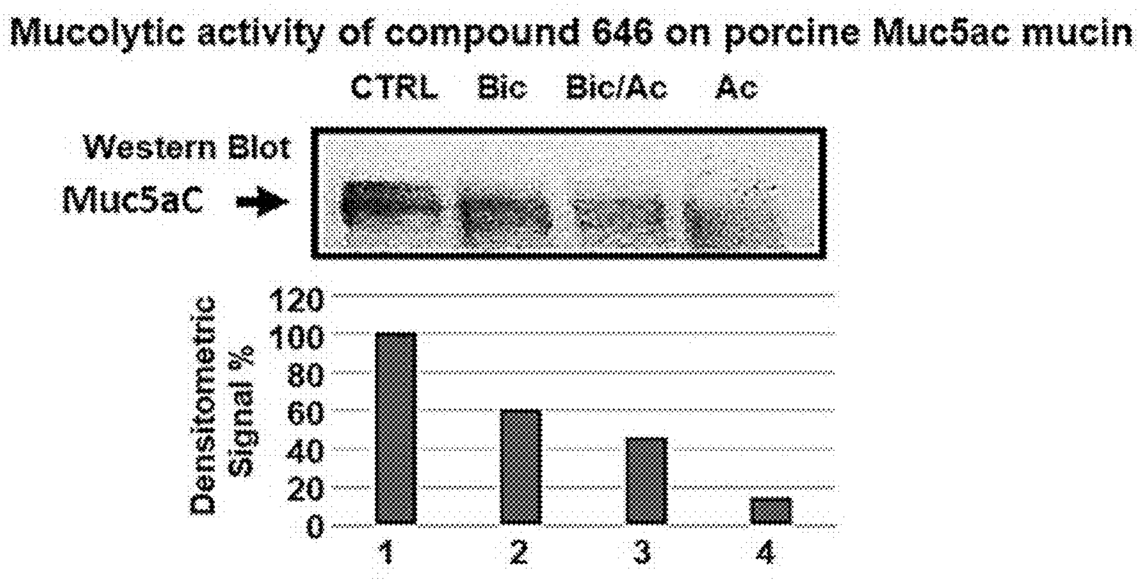
FIG. 12 demonstrates the mucolytic effect of compound 646 on Muc5ac mucin from porcine airway mucus. (Upper panel) Identification of Muc5ac mucin (black arrow) by western blot, from airway mucus sample collected in $HCO_3$-Ringer and treated with or without 2 mM of compound 646 for 30 mins at 37° C. Lane CTRL, untreated sample as control. Lane Bic, sample treated with compound preincubated in $HCO_3$-Ringer; lane Bic/Ac, sample treated with compound preincubated with 1:1 $HCO_3$-Ringer/Acetic acid 0.1N; lane Ac, sample treated with compound preincubated in acetate buffer 1M, pH 4.5. Lower panel, densitometric analysis of the protein bands identified with the Muc5ac mucin antibody. Densitometric signal of the sample control (CTRL) was normalized as 100% (% arbitrary units).
Figure 13:
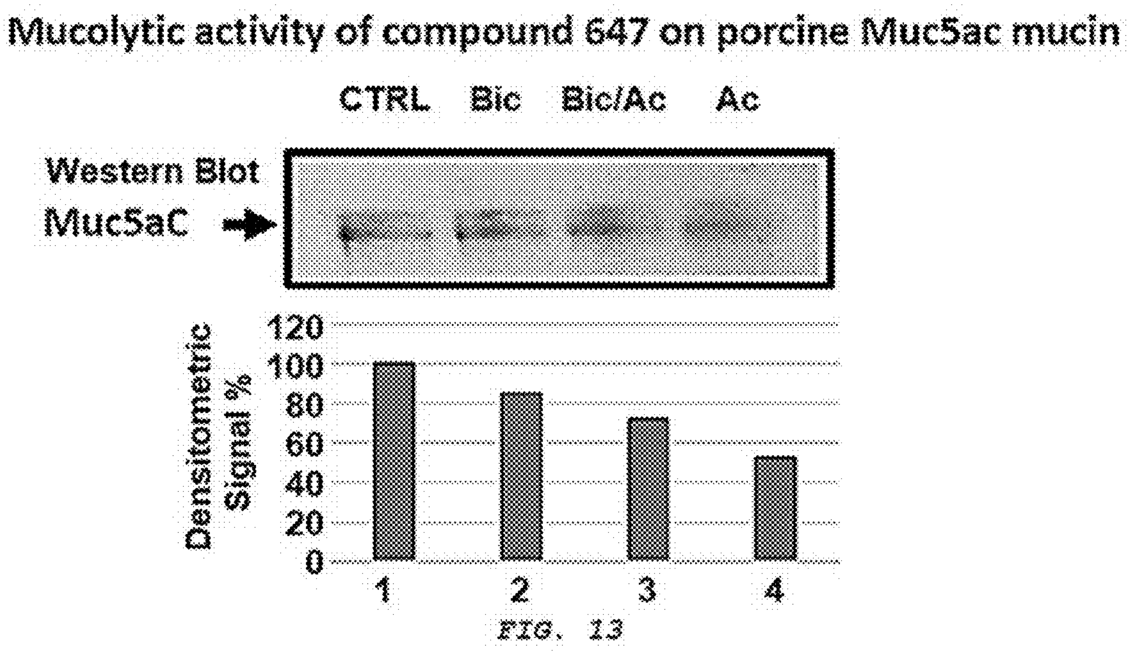
FIG. 13 demonstrates the mucolytic effect of compound 647 on Muc5ac mucin from porcine airway mucus. (Upper panel) Identification of Muc5ac mucin (black arrow) by western blot, from airway mucus sample collected in $HCO_3$-Ringer and treated with or without 2 mM of compound 647 for 30 mins at 37° C. Lane CTRL, untreated sample as control. Lane Bic, sample treated with compound preincubated in $HCO_3$-Ringer; lane Bic/Ac, sample treated with compound preincubated with 1:1 $HCO_3$-Ringer/Acetic acid 0.1N; lane Ac, sample treated with compound preincubated in acetate buffer 1M, pH 4.5, as described under Methods. Lower panel, densitometric analysis of the protein bands identified with the Muc5ac mucin antibody. Densitometric signal of the sample control (CTRL) was normalized as 100% (% arbitrary units). Control is pH 8, Bic 7.4, Bic/AC 6.9 AND AC 6.2
Figure 14:
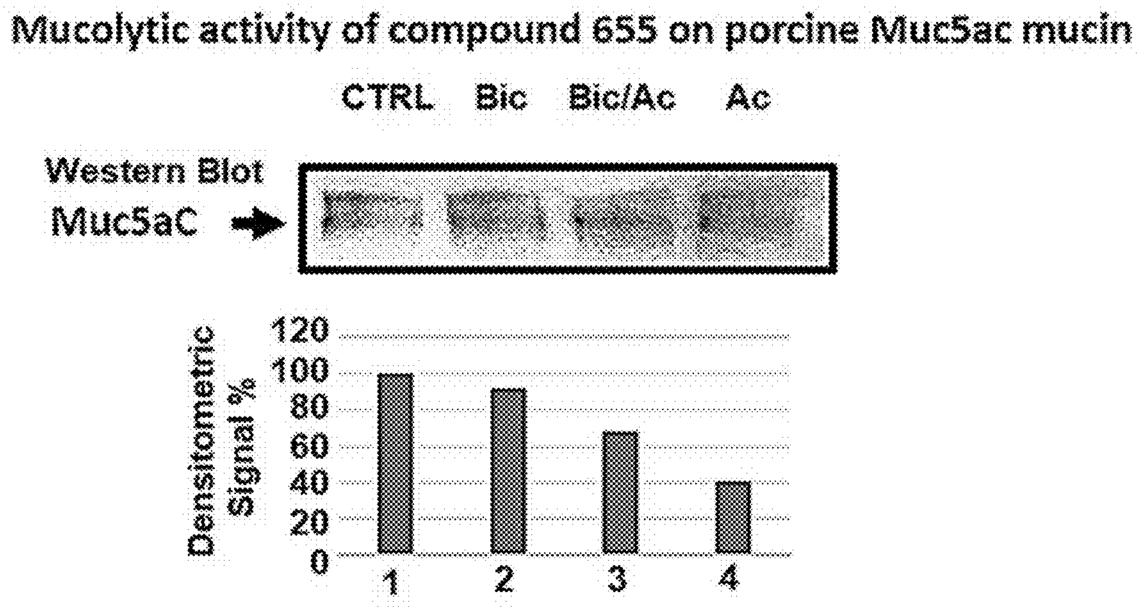
FIG. 14 demonstrates the mucolytic effect of compound 655 on Muc5ac mucin from porcine airway mucus. (Upper panel) Identification of Muc5ac mucin (black arrow) by western blot, from airway mucus sample collected in $HCO_3$-Ringer and treated with or without 2 mM of compound 655 for 30 mins at 37° C. Lane CTRL, untreated sample as control. Lane Bic, sample treated with compound preincubated in $HCO_3$-Ringer; lane Bic/Ac, sample treated with compound preincubated with 1:1 $HCO_3$-Ringer/Acetic acid 0.1N; lane Ac, sample treated with compound preincubated in acetate buffer 1M, pH 4.5. Lower panel, densitometric analysis of the protein bands identified with the Muc5ac mucin antibody. Densitometric signal of the sample control (CTRL) was normalized as 100% (% arbitrary units).
Figure 15:
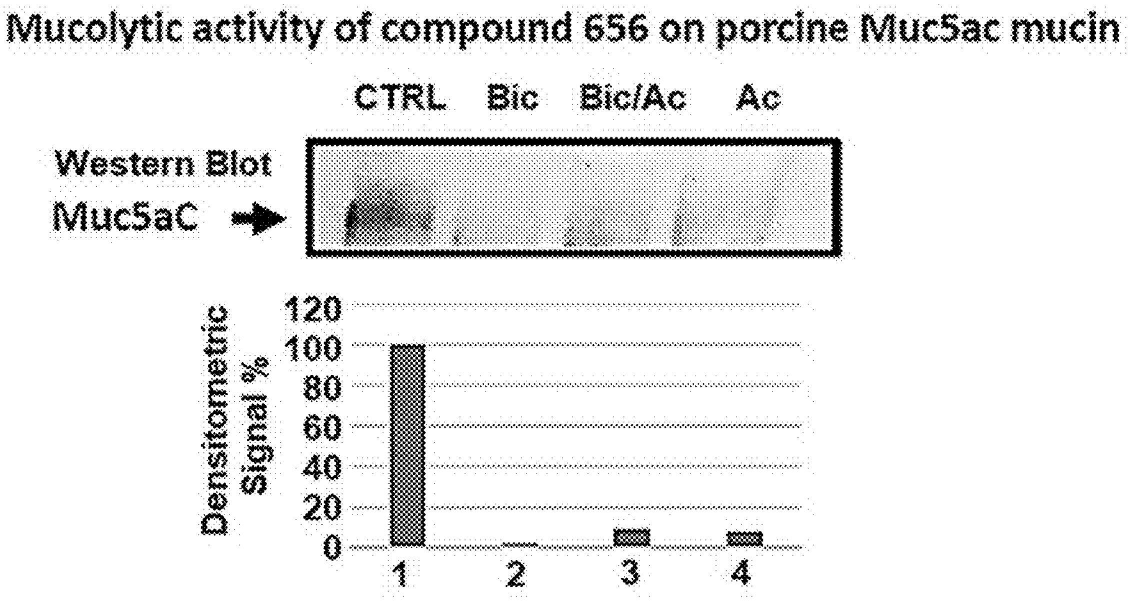
FIG. 15 shows the mucolytic effect of compound 656 on Muc5ac mucin from porcine airway mucus. (Upper panel) Identification of Muc5ac mucin (black arrow) by western blot, from airway mucus sample collected in $HCO_3$-Ringer and treated with or without 2 mM of compounds 656 for 30 mins at 37° C. Lane CTRL, untreated sample as control. Lane Bic, sample treated with compound preincubated in $HCO_3$-Ringer; lane Bic/Ac, sample treated with compound preincubated with 1:1 $HCO_3$-Ringer/Acetic acid 0.1N; lane Ac, sample treated with compound preincubated in acetate buffer 1M, pH 4.5. Lower panel, densitometric analysis of the protein bands identified with the Muc5ac mucin antibody. Densitometric signal of the sample control (CTRL) was normalized as 100% (% arbitrary units).

Additional studies with cysteamine and 2-aminoethane-1-d-1-thiol hydrochloride (Compound 646) indicated that cysteamine and Compound 646 had anti-mucin effect against gastric mucin, Muc5ac in particular, based upon mass spectrometry analysis of mucins separated on tris-glycine gels (e.g., see FIG. 7 and FIG. 8). In experiments with mucus collected from porcine airways, it was found that Compound 646 exerted a mucolytic effect, similar to cysteamine, on airway mucus (e.g., see FIG. 9). Further, the mucolytic effect of cysteamine can be enhanced when acidic conditions are used (e.g., see FIG. 10). In experiments using mucin extracted from porcine guts, the mucolytic effect of cysteamine was also found to be dose dependent (e.g., see FIG. 11).

Figure 16:
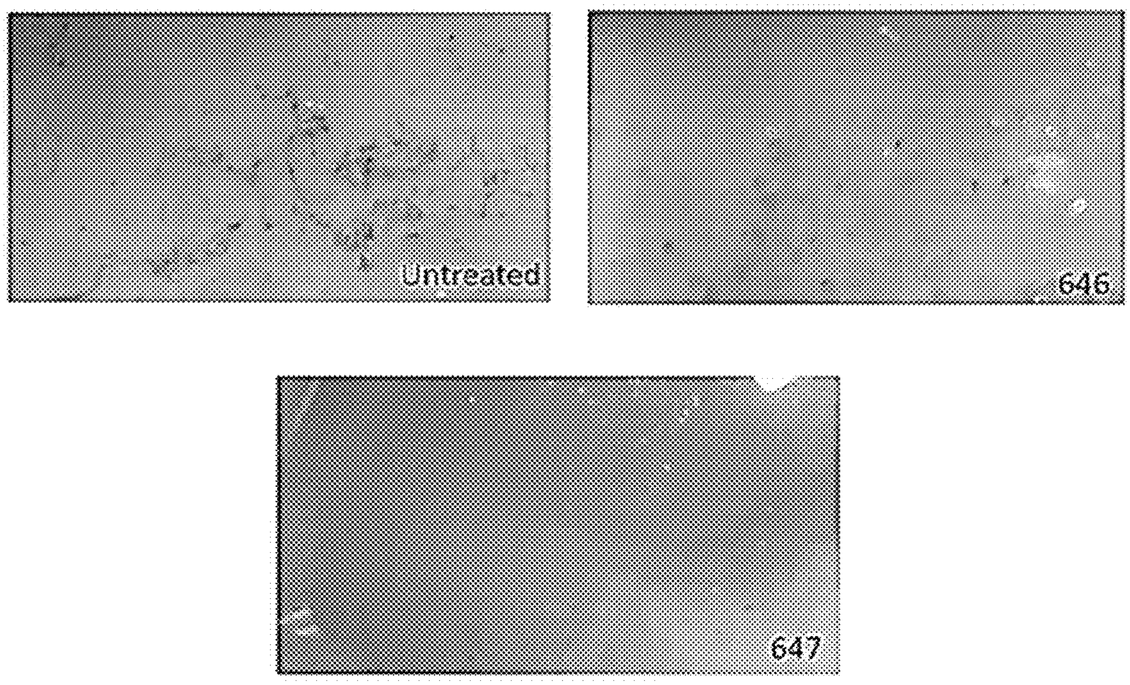
FIG. 16 provides the mucolytic activity of compounds 646 and 647 on respiratory secreted mucus. Small sections of open porcine trachea (~2 $cm^2$) were covered with $HCO_3$-Ringer solution (250 mL) containing $PGE_2$ (1 uM) and alcian blue (0.02%), with or without compounds at a 2 mM final concentration, and then incubated for 10 minutes at 37° C. Untreated section of trachea showed the presence of clusters of secreted mucus. In contrast, trachea sections treated with compounds 646 and 647 showed the presence of dispersed secreted mucus.
Figure 17:
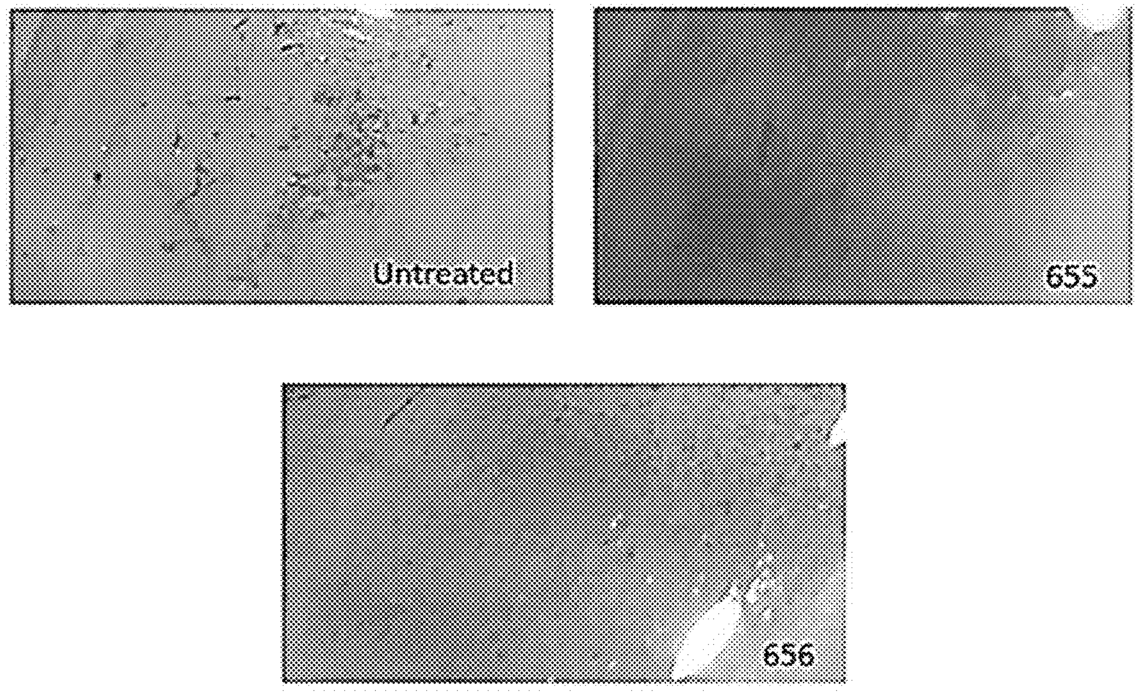
FIG. 17 provides the mucolytic activity of compounds 655 and 656 on respiratory secreted mucus. Small sections of open porcine trachea (~2 $cm^2$) were covered with $HCO_3$-Ringer solution (250 mL) containing $PGE_2$ (1 uM) and alcian blue (0.02%), with or without compounds at a 2 mM final concentration, and then incubated for 10 minutes at 37° C. Untreated section of trachea showed the presence of clusters of secreted mucus. In contrast, trachea sections treated with compounds 655 and 656 showed the presence of dispersed secreted mucus.
Figure 18:
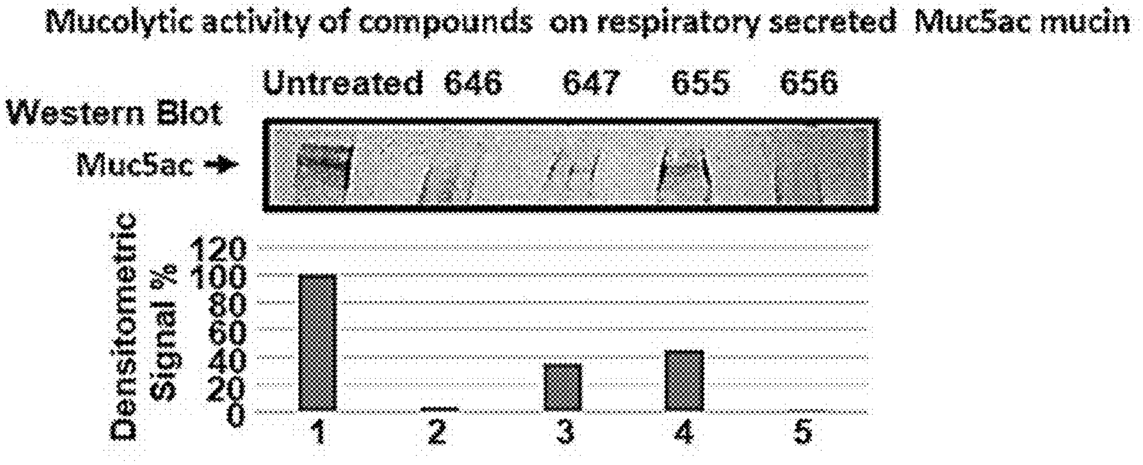
FIG. 18 provides the mucolytic activity of compounds on secreted Muc5ac mucin. Epithelial luminal surface of open porcine trachea sections (~2 $cm^2$) were covered with $HCO_3$-Ringer solution (250 mL) containing $PGE_2$ (1 uM), and alcian blue (0.02%), with or without compounds at a 2 mM final concentration, and incubated for 10 minutes at 37° C. Equal volumes of each collected sample were separated on vertical electrophoresis, and then transfer to an immobilon-P membrane for western blot analysis. Upper panel showed the identification of Muc5ac mucin from untreated and treated samples. Lower panel showed the densitometry analysis of the corresponding Muc5ac mucin band signal. Densitometric signal of the untreated sample, as control, was normalized to 100% (% arbitrary units).
Figure 19:
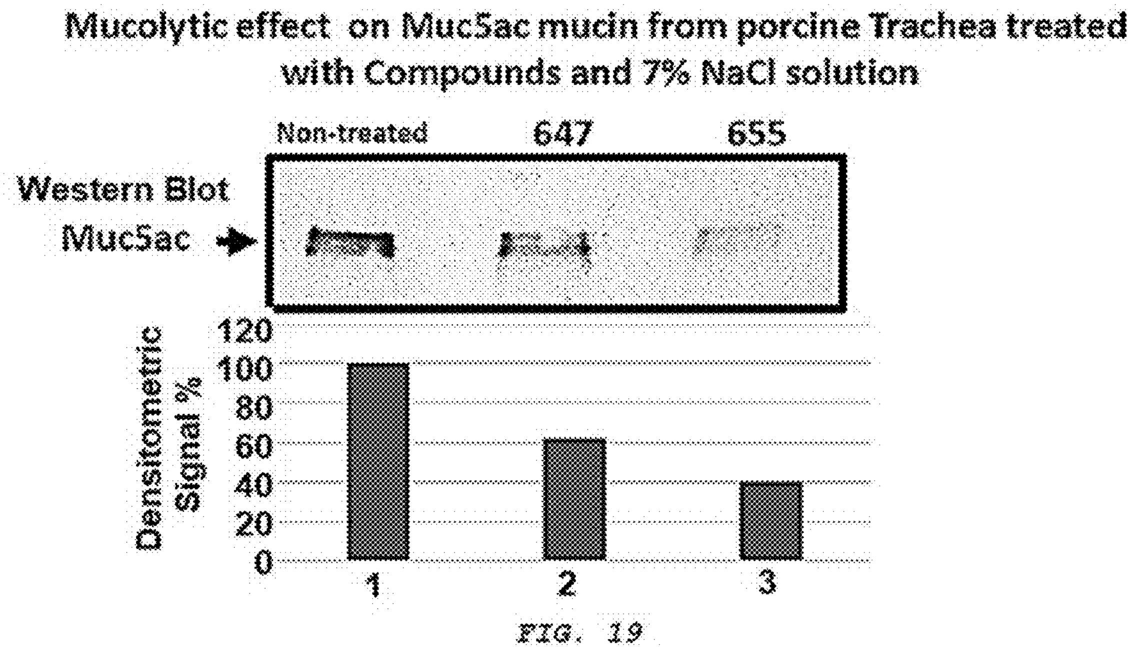
FIG. 19 demonstrates the mucolytic activity of compounds on secreted Muc5ac mucin. Epithelial luminal surface of open porcine trachea sections (~2 $cm^2$) were covered with 140 mL of $HCO_3$-Ringer solution containing $PGE_2$ (1 uM), in the presence or absence of compounds at a 2 mM final concentration, and incubated for 5 minutes at 37° C. Afterwards, 140 mL of sterile 7% NaCl inhaled solution was added and incubated for another 5 mins at 37° C. Equal volumes of each collected sample were separated on vertical electrophoresis, and then transferred to an immobilon-P membrane for western blot analysis. Upper panel showed the identification of Muc5ac mucin from untreated and treated samples with compound 647 and 655 separately. Lower panel showed the densitometry analysis of the western blot protein band signal corresponding to Muc5ac mucin. Densitometric signal of the non-treated sample, as control, was normalized to 100% (% arbitrary units).

Additional studies looked at the effect of acidic and basic conditions on the mucolytic activity of various deuterated cysteamine compounds (2-aminoethane-1-d-1-thiol hydrochloride (Compound 646), 2-mercaptoethan-2,2-$d_2$-1-aminium chloride (Compound 656)) and deuterated cystamine compounds (2,2'-disulfanediylbis(ethan-2-d-1-amine) dihydrochloride (Compound 647), 2,2'-disulfanediylbis(ethan-2,2-$d_2$-1-aminium) chloride (Compound 655)) on porcine Muc5ac mucin (e.g., see FIGS. 12-15). These studies indicate that the mucolytic activity of the deuterated compounds is enhanced under acidic conditions. Further studies looking at the mucolytic activity of Compound 646 and Compound 647 on respiratory secreted mucus by open porcine trachea indicated that the compounds dispersed clusters of secreted mucus, unlike the untreated samples (e.g., see FIG. 16). Similar results were seen when open porcine trachea samples were treated with Compound 655 and Compound 656 (e.g., see FIG. 17). Immunoblots for Muc5ac mucin, indicate that the compounds (Compound 646, Compound 647, Compound 655, Compound 656) decreased native Muc5ac levels on the epithelial luminal surfaces of the open porcine trachea sections (e.g., see FIG. 18). FIG. 19 further demonstrates that the deuterated cystamine compounds (Compound 647 and Compound 655) consistently works well in breaking down the mucus. It should be noted that the foregoing deuterated compounds (Compound 646, Compound 647, Compound 655, Compound 656) all work in dispersing mucus and lowering Muc5ac levels. For example, Compound 655 shows better mucolytic activity than Compound 647.

In view of the foregoing studies and results, there is a clear indication that cysteamine, deuterated cysteamine compounds, cystamine, and deuterated cystamine compounds are effective mucolytics. The strong correlation between the in vitro and ex vivo results with porcine lung airways and the use of said compounds in treating obstructive respiratory diseases in subjects, including human patients, is clearly indicated.

The compositions and methods presented herein provide straightforward approach to treat a broad spectrum of obstructive respiratory diseases by reducing the molecular weight of mucin gel polymers. In a particular embodiment, the disclosure provides for the treatment of a respiratory obstructive disease in a subject in need thereof, comprising administering to the subject a pharmaceutically acceptable composition comprising an effective amount of a compound having the structure of Formula I:

Formula I

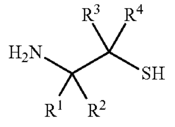

or a pharmaceutically acceptable salt, solvate, or prodrug thereof, wherein:

$R^1$-$R^4$ are independently selected from H or D. In a further embodiment, at least one of $R^1$-$R^4$ is D. In other embodiments, at least at least one of $R^1$-$R^4$ has deuterium enrichment of no less than about 10%, 50%, 90%, or 98%. In another embodiment, the pharmaceutical composition comprising cysteamine or the compound having structure of Formula I is formulated for oral administration.

In a further embodiment, the disclosure also provides for the treatment of a respiratory obstructive disease in a subject in need thereof, comprising administering to the subject a pharmaceutically acceptable composition comprising an effective amount of a compound having the structure of Formula II:

Formula II

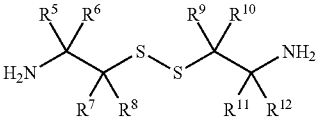

or a pharmaceutically acceptable salt, solvate, or prodrug thereof, wherein: $R^5$-$R^{12}$ are independently selected from H or D. In a further embodiment, at least one (e.g., 2, 3, 4, 5, 6, 7 or 8) of $R^5$-$R^{12}$ is D. In other embodiments, at least at least one (e.g., 2, 3, 4, 5, 6, 7 or 8) of $R^5$-$R^{12}$ has deuterium enrichment of no less than about 10%, 50%, 90%, or 98%. In another embodiment, the pharmaceutical composition comprising cystamine or the compound having structure of Formula II is formulated to be administered by inhalation. In a further embodiment, the pharmaceutical composition comprising cystamine or the compound having structure of Formula II has a pH of >7.0. In yet another embodiment, a second pharmaceutical composition that has a pH<7.0 is administered by inhalation after the pharmaceutical composition comprising cystamine or the compound having structure of Formula II is administered by inhalation. In yet another embodiment, the second pharmaceutical composition comprises hyperosmolar 3% saline. In another embodiment, the pharmaceutical composition comprising cystamine or the compound having structure of Formula II and/or the second pharmaceutical composition is administered by nebulization.

In yet a further embodiment, the disclosure also provides for the treatment of a respiratory obstructive disease in a subject in need thereof, comprising: (1) administering to the subject a pharmaceutically acceptable composition comprising an effective amount of a compound having the structure of Formula I:

Formula I

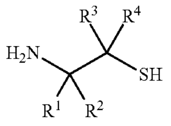

or a pharmaceutically acceptable salt, solvate, or prodrug thereof, wherein: $R^1$-$R^4$ are independently selected from H or D; and (2) administering to the subject a pharmaceutically acceptable composition comprising an effective amount of a compound having the structure of Formula II:

Formula II

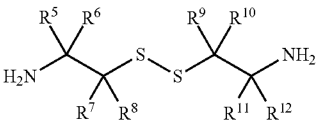

or a pharmaceutically acceptable salt, solvate, or prodrug thereof, wherein: $R^5$-$R^{12}$ are independently selected from H or D. In other embodiments, at least at least one (e.g., 2, 3, 4, 5, 6, 7 or 8) of $R^1$-$R^{12}$ has deuterium enrichment of no less than about 10%, 50%, 90%, or 98%. In another embodiment, the pharmaceutical composition comprising cysteamine or the compound having structure of Formula I is formulated for oral administration. In another embodiment, the pharmaceutical composition comprising cystamine or the compound having structure of Formula II is formulated for to be administered by inhalation. In a further embodiment, the pharmaceutical composition comprising cystamine or the compound having structure of Formula II has a pH of >7.0. In yet another embodiment, the pharmaceutical composition comprising cystamine or the compound having structure of Formula II is administered by inhalation to the subject which is followed by administration by inhalation of a second pharmaceutical composition that has a pH<7.0. In yet another embodiment, the second pharmaceutical composition comprises hyperosmolar 3% saline. In another embodiment, the pharmaceutical composition comprising cystamine or the compound having structure of Formula II and/or the second pharmaceutical composition is administered by nebulization.

In a further embodiment, a compound disclosed herein is substantially a single enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, Substantially an individual diastereomer, or a mixture of about 90% or more by weight of an individual diastereomer and about 10% or less by weight of any other diastereomer.

In a certain embodiment, a compound disclosed herein having the structure of Formula I is selected from:

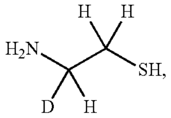, 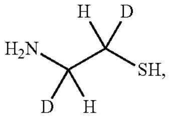, 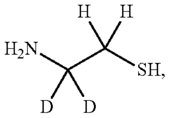, 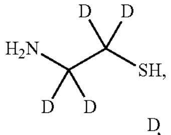, 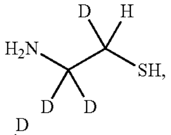, 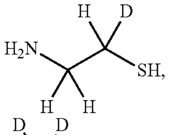, 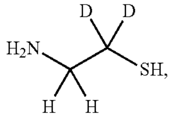, and 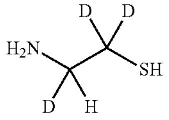

or a pharmaceutically acceptable salt, solvate, or prodrug thereof. In a further embodiment, a compound disclosed herein having the structure of Formula I is selected from:

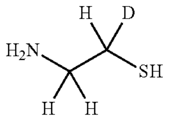 and 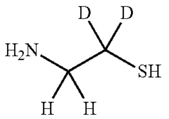

or a pharmaceutically acceptable salt, solvate, or prodrug thereof.

In another embodiment, a compound disclosed herein having a structure of Formula II is selected from:

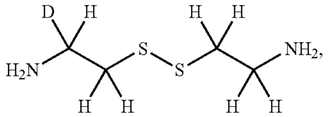
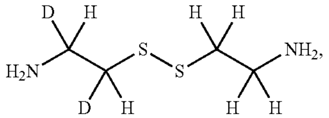
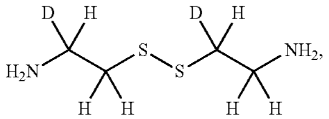
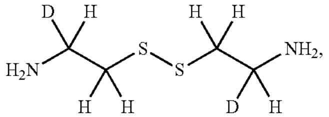
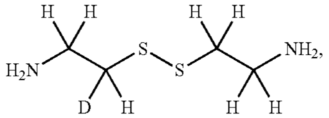
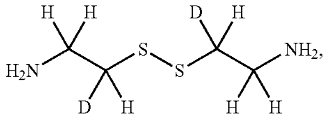
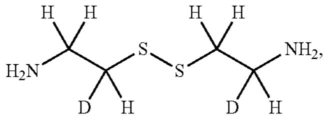
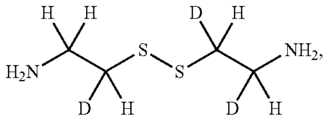
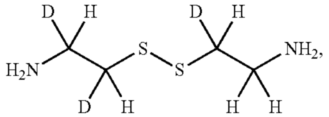
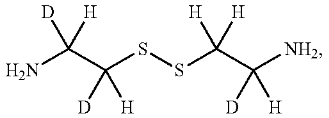
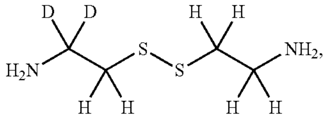
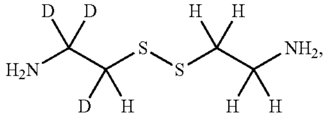
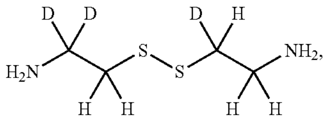
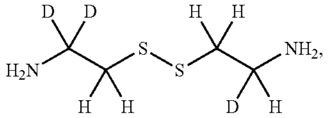
-continued
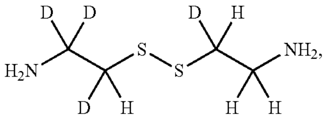
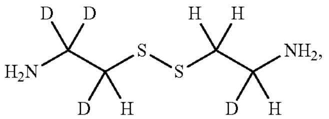
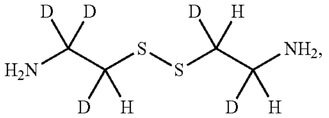
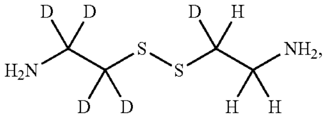
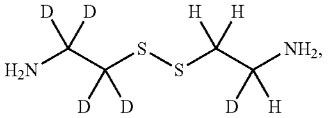
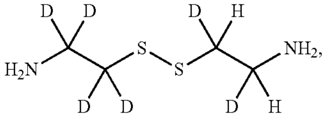
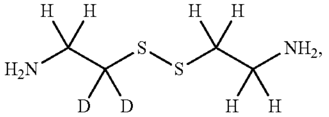
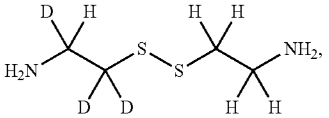
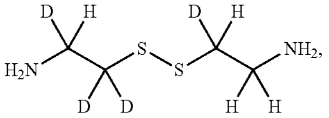
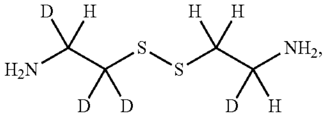
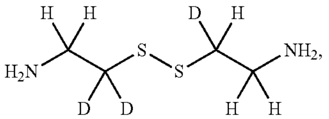
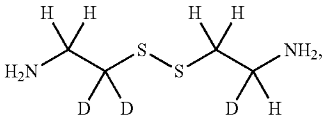
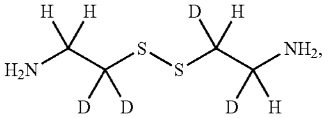
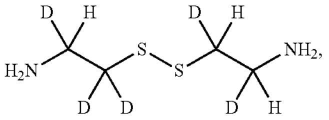

-continued

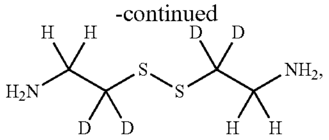

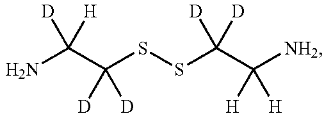

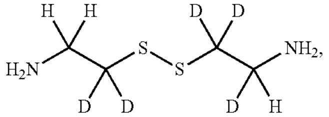

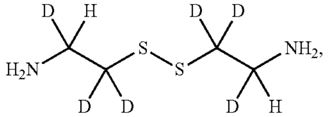

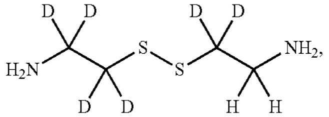

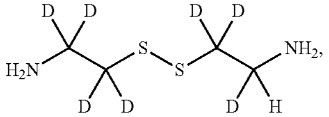

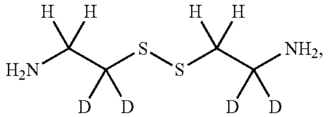

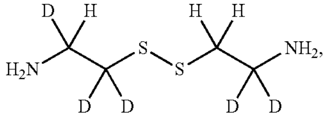

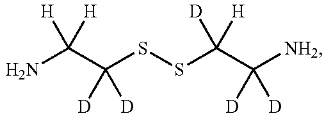

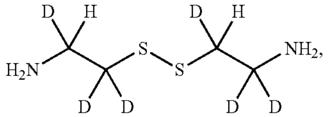

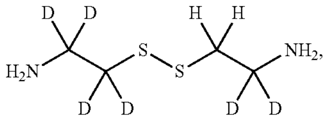

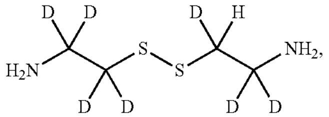

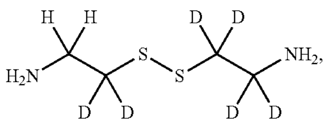

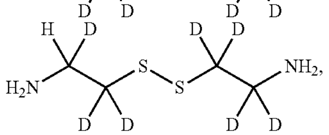

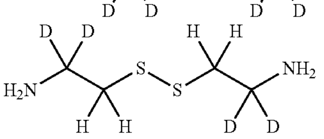

and

-continued

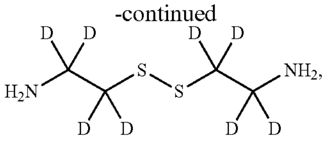

or a pharmaceutically acceptable salt, solvate, or prodrug thereof. In yet a further embodiment, a compound disclosed herein having a structure of Formula II is selected from

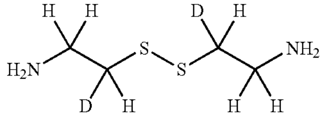

and

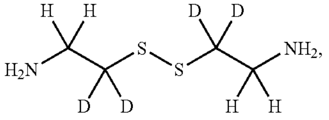

or a pharmaceutically acceptable salt, solvate, or prodrug thereof.

The disclosure is not limited with respect to a specific cysteamine or cystamine pharmaceutically acceptable salt. Further, the pharmaceutical compositions of the disclosure can contain cysteamine or cystamine individually, or combination of cysteamine and cystamine. The active agents in the composition, i.e., cysteamine or cystamine or compounds having the structure of Formula I or Formula II, may be administered in the form of a pharmacologically acceptable salt, ester, amide, prodrug or analog or as a combination thereof. Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula R—COOH where R is alkyl, and typically is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

While it may be possible for the compounds of the disclosure to be administered as the raw chemical, it is also possible to present them as a pharmaceutical composition.

Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington. The Science and Practice of Pharmacy, supra; Modified-Release Drug Delivery Technology, Rathbone et al., Eds. Drugs and the Pharmaceutical Science, Marcel Dekker, Inc.: New York, N.Y., 2002; Vol. 126).

The compositions include those suitable for oral, parenteral (including Subcutaneous, intradermal, intramuscular, intravenous, intraarticular, and intramedullary), intraperitoneal, transmucosal, transdermal, rectal and topical (including dermal, buccal, Sublingual and intraocular) and via inhaled administration. The most suitable route for administration depends on a variety of factors, including interpatient variation or disorder type, and therefore the disclosure is not limited to just one form of administration. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping or otherwise preparing the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, Carbopol gel, polyethylene glycol, and/or titanium dioxide, lacquer Solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations Suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator. Preferred unit dosage formulations are those containing an effective dose, as herein below recited, or an appropriate fraction thereof, of the active ingredient.

There are notable advantages to administering a compound disclosed herein by inhalation for treating an obstructive pulmonary disease: (1) inhalation doses are generally smaller than systemic doses; (2) onset of effect is faster with inhalation than with oral administration; (3) the drug is delivered directly to the target organ (lung) or airways, with minimized systemic exposure; (4) systemic adverse effects are less severe and less frequent with inhalation than with systemic drug delivery (injection or oral); and (5) inhaled drug therapy is painless and relatively comfortable.

In a particular embodiment, the disclosure provides methods and therapies for treating a subject having an obstructive respiratory disease comprising administering by inhalation a pharmaceutical composition comprising a compound disclosed herein. In a further embodiment, the pharmaceutical composition comprising the compound of the disclosure for administration by inhalation has a neutral or slightly basic pH (e.g., comprises bicarbonate). In yet a further embodiment, the disclosure further provides for the administration by inhalation of a second pharmaceutical composition which comprises saline that has been adjusted to have weakly acidic pH (e.g., pH 4.5 to pH 6.8), wherein the second pharmaceutical composition is administered a short period of time (e.g., 1 second to 1 minute, 1 min to 5 min, 5 min to 10 min, 10 min to 15 min, 15 min to 30 min, 30 min to 45 min, 45 min to 1 hours or any period of time between any of the foregoing values) after the pharmaceutical composition comprising a compound of the disclosure. Various commercially available nebulizers and inhalation devices can be used to administer a compound of the disclosure, including those made by PARI, Briutcare, Omron, and Flyp. Where the method of treating a subject includes administering both oral and inhaled compositions of the disclosure, the total dose can be appropriately split between the two routes of administration such that the appropriate total dose is as described below.

In another embodiment, the disclosure also provides methods and therapies for treating a subject having an obstructive respiratory disease comprising: administering by inhalation a first pharmaceutical composition comprising a cysteamine-based compound or cystamine-based compound disclosed herein, optionally, administering by inhalation a third pharmaceutical composition comprising a hyperosmolar 3% saline solution (pH 5.0); administering by oral or parenteral administration a second pharmaceutical composition comprising a cysteamine-based compound or cystamine-based compound disclosed herein; wherein if the third pharmaceutical composition is administered, then it is administered within a short period time after the administration of the first pharmaceutical composition.

In another embodiment, the first pharmaceutical composition comprises a cystamine-based compound. In yet another embodiment, the first pharmaceutical composition comprises Compound 647 or Compound 655. In a further embodiment, the second pharmaceutical composition is formulated for oral delivery and comprises a cysteamine-based compound. In yet a further embodiment, the second pharmaceutical composition is formulated for oral delivery and comprises Compound 646 or Compound 656.

In various embodiments of the disclosure, a compound of the disclosure is administered to a subject at a daily dose ranging from about 10 mg/kg to about 2.5 g/kg, or from about 100 mg/kg to about 250 mg/kg, or from about 60 mg/kg to about 100 mg/kg or from about 50 mg/kg to about 90 mg/kg, or from about 30 mg/kg to about 80 mg/kg, or from about 20 mg/kg to about 60 mg/kg, or from about 10 mg/kg to about 50 mg/kg. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg or 1000 mg/kg, or may range between any two of the foregoing values. In some embodiments, the compound of the disclosure is administered at a total daily dose of from approximately 0.25 $g/m^2$ to 4.0 $g/m^2$ body surface area, about 0.5-2.0 $g/m^2$ body surface area, or 1-1.5 $g/m^2$ body surface area, or 1-1.95 $g/m^2$ body surface area, or 0.5-1 $g/m^2$ body surface area, or about 0.7-0.8 $g/m^2$ body surface area, or about 1.35 $g/m^2$ body surface area, or about 1.3 to about 1.95 $grams/m^2/day$, or about 0.5 to about 1.5 $grams/m^2/day$, or about 0.5 to about 1.0 $grams/m^2/day$, e.g., at least about 0.3, 0.4, 0.5, 0.6, 0.7, 0.8, 0.9, 1.0, 1.1, 1.2, 1.3, 1.4, 1.5, 1.6, 1.7, 1.8, 1.9 or 2 $g/m^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, 3.25, 3.5 or 3.75 $g/m^2$ or may range between any two of the foregoing values. In any of the foregoing embodiments, the subject has an obstructive respiratory disease. In still another embodiment of the foregoing the subject has COPD or cystic fibrosis. In still another of further embodiment of any of the foregoing, the subject has airway obstruction caused by abnormal mucus accumulation.

The compounds can be administered in various modes, e.g. orally, inhalation, or injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday'). Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

In some embodiments, the disclosure provides for a delayed and/or extended release oral formulation which comprises an enteric coating that releases a compound disclosed herein when the formulation reaches the small intestine or a region of the gastrointestinal tract of a subject in which the pH is greater than about pH 4.5. In various embodiments, the formulation releases at a pH of about 4.5 to 6.5, 4.5 to 5.5, 5.6 to 6.5 or about pH 4.5, 5.0, 5.5, 6.0 or 6.5. In one embodiment, the formulation provides for release beginning in the upper small intestine to the lower small intestine. For example, U.S. Pat. Nos. 8,026,284; 9,192,590; 9,198,882; 9,511,039; 9,814,689; 9,795,578; 9,750,708; 9,925,156; 9,925,157; 9,925,158; 10,485,774; and 9,173, 851 (the disclosure of which are incorporated herein) describe various delayed release formulations of cysteamine and cystamine.

In a particular embodiment, the compound of the disclosure or a pharmaceutically acceptable salt, prodrug or solvate thereof is formulated for oral administration (e.g., as a capsule, table, caplet, solution, etc.). In a further embodiment, the disclosure provides for capsules, tablets, or caplets, comprising 50 mg to 200 mg of a compound of disclosure or a pharmaceutically acceptable salt (e.g., a bitartrate salt), prodrug or solvate thereof. In yet a further embodiment, the capsules, tablets, or caplets further comprise inactive ingredients, such as colloidal silicon dioxide, croscarmellose sodium, D&C yellow no. 10 aluminum lake, FD&C blue no. 1 aluminum lake, FD&C blue no. 2 aluminum lake, FD&C red no. 40 aluminum lake, gelatin, magnesium stearate, microcrystalline cellulose, pharmaceutical glaze, pregelatinized starch, silicon dioxide, sodium lauryl sulfate, synthetic black iron oxide and/or titanium dioxide.

In yet another embodiment, a compound disclose herein is administered at a frequency of 4 or less times per day (e.g., one, two or three times per day). In various embodiments, the composition is a delayed or controlled release dosage form that provides increased delivery of a compound disclosed herein to the small intestine.

In an embodiment, the compound of the disclosure or a pharmaceutically acceptable salt, prodrug or solvate thereof is formulated for oral administration (e.g., as a capsule, table, caplet, solution, etc.) that provides for delayed release. In a further embodiment, the disclosure provides for delayed release capsules, tablets, or caplets, comprising 25 mg to 75 mg of a compound of disclosure or a pharmaceutically acceptable salt (e.g., a bitartrate salt), prodrug or solvate thereof. In yet a further embodiment, the delayed release capsules, tablets, or caplets further comprise inactive ingredients, such as microcrystalline cellulose, Eudragit® L 30 D-55, Hypromellose, talc, triethyl citrate, sodium lauryl sulfate, purified water, gelatin, titanium dioxide, blue ink and/or white ink.

The delay or controlled release form can provide a $C_{max}$ of a compound disclosed herein, or a biologically active metabolite thereof, that is at least about 35%, 50%, 75% or higher than the $C_{max}$ provided by an immediate release dosage form containing the same amount of the compound. In another embodiment, the delay and extended release formulation provides an improved AUC compared to immediately release forms of the compound. For example, the AUC is increased compared to an immediate release formulation. In yet another embodiment, the delayed or controlled release dosage form comprises an enteric coating that releases a compound disclosed herein when the composition reaches the small intestine or a region of the gastrointestinal tract of a subject in which the pH is greater than about pH 4.5. In various embodiments, the pH is between 4.5 and 6.5. In one embodiment, the pH is about 5.5 to 6.5. In one embodiment the compound of the disclosure is delivered throughout the small intestine providing an extended release in the small intestine.

In various embodiments, the enterically coated formulation comprising a compound of the disclosure is granulated and the granulation is compressed into a tablet or filled into a capsule. In certain embodiments, the granules are enterically coated prior to compressing into a tablet or capsule. Capsule materials may be either hard or soft, and are typically sealed, such as with gelatin bands or the like. Tablets and capsules for oral use will generally include one or more commonly used excipients as discussed herein.

A suitable pH-sensitive polymer is one which will dissolve in intestinal environment at a higher pH level (pH greater than 4.5), such as within the small intestine and therefore permit release of the pharmacologically active substance in the regions of the small intestine and not in the upper portion of the GI tract, such as the stomach.

In various embodiments, exemplary formulations comprising a compound of the disclosure that are contemplated for use in the present methods include those described in International Patent Applications PCT/US2007/002325, PCT/US2014/042607 and PCT/US2014/042616 (the disclosure of which are incorporated herein by reference).

For administration of the dosage form, i.e., the tablet or capsule comprising the enterically coated compound of the disclosure (e.g., a deuterated compound of the disclosure), a total weight in the range of approximately 50 mg to 1000 mg is used. In various embodiments, the tablet or capsule comprises 25, 50, 75, 100, 125, 150, 175, 200, 225, 250, 275, 300, 400 or 500 mg active ingredient, and multiple tablets or capsules are administered to reach the desired dosage. The dosage form is orally administered to a subject in need thereof.

In one embodiment, a tablet core comprises about 50 mg of a compound of the disclosure that is encapsulated in an enteric coating material having a thickness of about 60-100 μm (e.g., about 71, 73, 75, 77, or 79 μm or any value there between) and/or about 10-13% (e.g., about 10.5, 11.0, 11.2, 11.4, 11.6, 11.8, 12.0, 12.2, 12.4, 12.6, 12.8% of any value there between) by weight of the tablet. In another embodiment, a tablet core comprises about 150 mg of a compound of the disclosure about that is encapsulated in an enteric coating material having a thickness of about 90-130 μm (e.g., about 97, 99, 101, 103, 105, 107, 109, 111, 113 μm or any value there between) and/or about 9-14% (e.g., about 9.5, 9.7, 9.9, 10.1, 10.3 10.5, 11.0, 11.2, 11.4, 11.6, 11.8, 12.0, 12.2, 12.4, 12.6, 12.8, 13.0, 13.2, 13.4, 13.6, 13.8% or any value there between) by weight of the tablet by weight of the tablet.

In any of the foregoing embodiments, the enteric coating material can be selected from the group comprising polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethyl cellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters. The composition can be administered orally or parenterally.

In addition, various prodrugs can be "activated" by use of the enterically coated compound of the disclosure. Prodrugs are pharmacologically inert, they themselves do not work in the body, but once they have been absorbed, the prodrug decomposes. The prodrug approach has been used successfully in a number of therapeutic areas including antibiotics, antihistamines and ulcer treatments. The advantage of using prodrugs is that the active agent is chemically camouflaged and no active agent is released until the drug has passed out of the gut and into the cells of the body. For example, a number of prodrugs use S—S bonds. Weak reducing agents, such as cysteamine, reduce these bonds and release the drug. Accordingly, the compositions of the disclosure are useful in combination with pro-drugs for timed release of the drug. In this aspect, a pro-drug can be administered followed by administration of an enterically coated compound of the disclosure (at a desired time) to activate the pro-drug.

Prodrugs of cysteamine have been described previously. See, e.g., Andersen et al., In vitro Evaluation of Novel Cysteamine Prodrugs Targeted to g-Glutamyl Transpeptidase (poster presentation), which describes S-pivaloyl cysteamine derivatives, S-benzoyl cysteamine derivatives, S-acetyl cysteamine derivatives and S-benzoyl cysteamine) glutamate-ethyl ester). Omran et al., Bioorg Med Chem Lett., 21(8):2502-4, 2011, describes a folate pro-drug of cystamine as a treatment for nephropathic cystinosis.

In any of foregoing embodiments, formulations for use in the methods described herein can comprise a pharmaceutically acceptable salt of the compound of the disclosure, such a bitartrate salt or hydrochloride salt, instead of free base compound.

The compounds disclosed herein may also be combined or used in combination with other agents, devices, and/or techniques useful in the treatment of obstructive respiratory diseases. Examples of such agents include, but are not limited to, mucolytic agents, antibiotics, anti-inflammatory medications, bronchodilators, and CFTR Modulator therapies. Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required. Examples of techniques and devices useful in the treatment of obstructive respiratory diseases include, but are not limited to, chest physical therapy, airway clearance techniques, vibrating vest, and oxygen therapy.

In a certain embodiment, the compounds disclosed herein can be combined with one or more mucolytic agents known in the art, including, but not limited to, acetylcysteine, ambroxol, bromhexine, carbocisteine, erdosteine, mecysteine, and dornase alfa.

In another embodiment, the compounds disclosed herein can be combined with one or more CFTR Modulator therapies known in the art, including, but not limited to, ivacaftor, tezacaftor, and lumacaftor.

In yet another embodiment, the compounds disclosed herein can be combined with one or more bronchodilators known in the art, including, but not limited to, albuterol, levalbuterol, ipratropium, aclidinium, arformoterol, formterol, indacaterol, salmeterol, and tiotropium.

In a further embodiment, the compounds disclosed herein can be combined with one or more anti-inflammatory medications known in the art, including, but not limited to, budesonide, fluticasone, beclomethasone, ciclesonide, flunisolide, mometasone, and triamcinolone.

It is to be understood that while the disclosure has been described in conjunction with specific embodiments thereof, that the foregoing description as well as the examples which follow are intended to illustrate and not limit the scope of the disclosure. Other aspects, advantages and modifications within the scope of the disclosure will be apparent to those skilled in the art to which the disclosure.

EXAMPLES

Materials. Commercial Crude Mucin extract from Porcine Stomach (M-2378), Prostaglandin E2, and all other chemicals were purchased from Sigma-Aldrich. Novex Gel 4-12% Tris-Glycine were purchased from Invitrogen, (Carlsbad, CA). Imperial Protein stain and Spectra multicolor broad range protein ladder from Thermo Scientific (Rockford, IL). Cysteamine bitartrate and cystamine were purchased from commercial vendors. Deuterated cysteamine and deuterated cystamine were synthesized as described below.

Chemical Synthesis of Isotopically Enriched $d_2$-cysteamine and $d_2$-cystamine tert-butyl (2-oxoethyl)carbamate 4

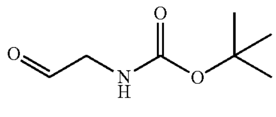

The title compound was prepared as described in Kathman et al. (*J. Am. Chem. Soc.*, 137(39):12442-12445 (2015)). Sodium periodate (9.40 g, 43.9 mmol, 1.20 equiv) was added to a suspension of tert-butyl (2,3-dihydroxypropyl)carbamate (7.00 g, 36.6 mmol, 1.00 equiv) in water (61.0 mL). The reaction was stirred in the dark at ambient temperature for 1 h. The reaction was filtered and the filtrate was extracted with chloroform (×4). The combined organic layers were dried over $MgSO_4$, filtered and concentrated to afford the title compound 4 as a yellow oil in 88% yield (5.12 g). The compound was used directly in the next step without further purification. $^{1}H$ NMR (600 MHz, $CDCl_3$) δ 9.66 (s, 1H), 5.18 (s, 1H), 4.08 (d, J=4.9 Hz, 2H), 1.45 (s, 9H) ppm.

Tert-butyl (2-hydroxyethyl-2-d)carbamate 5

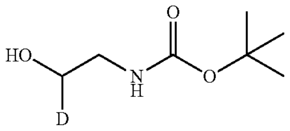

At 0° C., sodium borodeuteride (1.62 g, 38.60 mmol, 1.20 equiv.) was added portionwise to a solution of 4 (5.12 g, 32.16 mmol, 1.00 equiv.) in methanol (41 mL). The reaction was stirred for 15 minutes at 0° C. and then 1 h at ambient temperature. Water was added and the resulting mixture was extracted with dichloromethane (3×). The combined organic layers were dried over $Na_2SO_4$, filtered and concentrated to afford compound 5 as colorless oil in 92% yield (4.78 g). The compound was used in the next step without further purification. $^{1}H$ NMR (600 MHz, $CDCl_3$) δ 5.17 (s, 1H), 3.62 (s, 1H), 3.29-3.20 (m, 3H), 1.41 (s, 11H) ppm. $^{13}C$ NMR (151 MHz, $CDCl_3$) δ 156.95, 79.70, 62.03 (t, J=21.1 Hz), 43.07, 28.46 ppm. HRMS ($ES^+$) calculated for $C_7H_{14}DNO_3Na$ $[M+Na]^+$ 185.1012, found 185.1009 IR (neat) ν 3346, 2978, 1683, 1516, 1366, 1249, 1165, 1098, 1056 $cm^{-1}$.

2-((tert-butoxycarbonyl)amino)ethyl-1-d 4-methylbenzenesulfonate 6

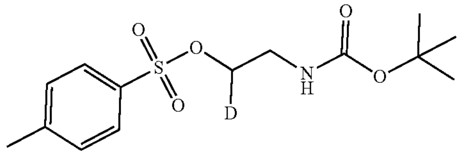 [SMILES: [2H]C(CNC(=O)OC(C)(C)C)OS(=O)(=O)c1ccc(C)cc1]

The title compound was prepared as described in Devine et al., (*ACS Infect. Dis.* 3 (3):225-236 (2017)). At 0° C., p-toluene sulfonyl chloride (2.57 g, 13.50 mmol, 1.46 equiv.) and triethylamine (2.53 mL, 18.11 mmol, 1.96 equiv.) were added to a solution of 5 (1.50 g, 9.24 mmol, 1.00 equiv.) in anhydrous dichloromethane (30 mL). The reaction was stirred at 0° C. for 10 minutes, then warmed and maintained at ambient temperature under stirring for 2 h. The reaction was concentrated and purified by silica gel column chromatography (0-20% ethyl acetate in hexanes) to give the desired compound 6 as colorless oil in 90% yield (2.62 g). $^{1}H$ NMR (600 MHz, $CDCl_3$) δ 7.77 (d, J=8.2 Hz, 2H), 7.34 (d, J=8.1 Hz, 2H), 4.88 (s, 1H), 4.03 (d, J=4.4 Hz, 1H), 3.36 (t, J=5.2 Hz, 2H), 2.43 (s, 3H), 1.39 (s, 9H) ppm. $^{13}C$ NMR (151 MHz, $CDCl_3$) δ 155.72, 145.23, 132.66, 130.07, 128.03, 79.87, 69.27 (t, J=22.7 Hz), 39.72, 28.38, 21.76 ppm. HRMS ($ES^+$) calculated for $C_{14}H_{20}DNO_5SNa$ $[M+Na]^+$ 339.1101, found 339.1099 IR (neat) ν 2976, 1695, 1513, 1363, 1248, 1173, 945, 814, 661, 552 $cm^{-1}$.

S-(2-((tert-butoxycarbonyl)amino)ethyl-1-d) ethanethioate 7

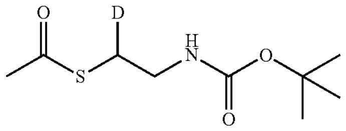

To a solution of potassium thioacetate (1.04 mg, 9.17 mmol, 2.00 equiv) in anhydrous dimethyl formamide (21.8 mL) at 0° C. was slowly added a solution of 6 (1.45 g, 4.58 mmol, 1.00 equiv) in anhydrous dimethyl formamide (7.3 mL). The reaction was stirred at 0° C. for 10 minutes, then heated to 50° C. for 90 minutes. The reaction was cooled to ambient temperature and water was added. The mixture was extracted with ethyl acetate (×3). The combined organic layers were washed with water (×2), brine, dried over $Na_2SO_4$, filtered and concentrated. The crude product was purified by silica gel column chromatography (0-20% of ethyl acetate in hexanes) to afford the title compound 7 as a brown oil in 56% yield (561 mg). $^{1}H$ NMR (600 MHz, $CDCl_3$) δ 4.87 (s, 1H), 3.32-3.21 (m, 2H), 2.96 (s, 1H), 2.32 (s, 3H), 1.40 (s, 9H) ppm. $^{13}C$ NMR (151 MHz, $CDCl_3$) δ 195.90, 155.88, 79.56, 40.23, 30.74, 29.16 (t, J=21.1 Hz), 28.44 ppm. HRMS ($ES^+$) calculated for $C_9H_{16}DNO_3SNa$ $[M+Na]^+$ 243.0890, found 243.0887. IR (neat) ν 3356, 2977, 2932, 1685, 1512, 1365, 1246, 1164, 1129, 954, 621 $cm^{-1}$.

Tert-butyl (2-mercaptoethyl-2-d)carbamate 8

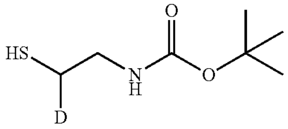

Di-tert-butyl (disulfanediylbis(ethane-2,1-diyl-2d)) dicarbamate 9

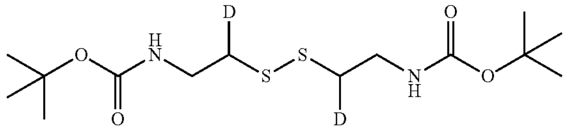 [SMILES: [2H]C(CNC(=O)OC(C)(C)C)SSC([2H])CNC(=O)OC(C)(C)C]

An aqueous solution of sodium hydroxide (10% wt, 4.30 mL) was added to a solution of 7 (340 mg, 1.54 mmol, 1.00 equiv) in methanol (8.60 mL). The reaction was stirred at ambient temperature for 40 minutes. Water was added and the mixture was extracted with ethyl acetate (×3). The combined organic layers were dried over $Na_2SO_4$, filtered and concentrated. The crude reaction was purified by silica gel column chromatography (0-20% of ethyl acetate in hexanes) to give both the tert-butyl (2-mercaptoethyl-2-d) carbamate (8) as a colorless oil in 61% yield (167 mg) and the di-tert-butyl (disulfanediylbis(ethane-2,1-diyl-2-d))dicarbamate (9) as an orange solid in 19% yield (53 mg).

Tert-butyl (2-mercaptoethyl-2-d)carbamate (8): $^{1}H$ NMR (600 MHz, $CDCl_3$) δ 4.98 (s, 1H), 3.32-3.22 (m, 2H), 2.60 (d, J=6.3 Hz, 1H), 1.42 (s, 9H), 1.32 (d, J=8.4 Hz, 1H) ppm. $^{13}C$ NMR (151 MHz, $CDCl_3$) δ 155.85, 79.60, 43.59, 28.46, 24.87 (t, J=21.1 Hz) ppm. HRMS ($ES^+$) calculated for $C_{14}H_{26}D_2N_2O_4S_2Na$ $[M+Na]^+$ 377.1514, found 377.1511 (detected as dimer) IR (neat) ν 3355, 2977, 2932, 1687, 1509, 1365, 1247, 1162 $cm^{-1}$.

Di-tert-butyl (disulfanediylbis(ethane-2,1-diyl-2-d))dicarbamate 9: $^{1}H$ NMR (600 MHz, $CDCl_3$) δ 5.11 (s, 2H), 3.41 (t, J=5.9 Hz, 4H), 2.75 (s, 2H), 1.41 (s, 18H) ppm. $^{13}C$ NMR (151 MHz, $CDCl_3$) δ 155.96, 79.58, 39.27, 38.16 (t, J=21.1 Hz), 28.47 ppm. HRMS ($ES^+$) calculated for $C_{14}H_{26}D_2N_2O_4S_2Na$ $[M+Na]^+$ 377.1514, found 377.1510 IR (neat) ν 3346, 2976, 2931, 1685, 1512, 1365, 1247, 1164 $cm^{-1}$.

Di-tert-butyl (disulfanediylbis(ethane-2,1-diyl-2-d))dicarbamate 11

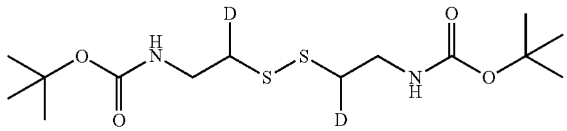 [SMILES: [2H]C(CNC(=O)OC(C)(C)C)SSC([2H])CNC(=O)OC(C)(C)C]

Sodium bicarbonate (267 mg, 3.17 mmol, 1.50 equiv) and iodine (321 mg, 1.27 mmol, 0.60 equiv) were added portionwise to a solution of tert-butyl (2-mercaptoethyl-2-d) carbamate (8, 376 mg, 2.11 mmol, 1.00 equiv) in methanol (15 mL). After 5 minutes, a saturated solution of sodium bicarbonate was added. The mixture was extracted with ethyl acetate (×3). The combined organic layers were washed with water, a solution of sodium thiosulfate (10 w.t, 4×50 mL), and brine; dried over $Na_2SO_4$; and then filtered and concentrated to afford the desired product in 91% (341 mg).

2-aminoethane-1-d-1-thiol hydrochloride 10

(Compound 646)

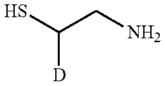

At 0° C., a solution of tert-butyl (2-mercaptoethyl-2-d) carbamate (8, 160 mg, 0.90 mmol, 1.00 equiv) in methanol (1.5 mL) was added to a solution containing HCl (4N in 1,4-dioxane, 6.50 mL). The reaction was stirred at ambient temperature for 1 hour. The reaction was concentrated to afford the desired compound in a quantitative yield as a white solid (102 mg). $^{1}H$ NMR (600 MHz, $D_2O$) δ 3.15 (d, J=6.5 Hz, 2H), 2.84-2.68 (m, 1H) ppm. $^{13}C$ NMR (151 MHz, $D_2O$ (+MeOH as the internal standard)) δ 42.50, 21.63 (t, J=21.1 Hz) ppm. HRMS ($ES^+$) calculated for $C_2H_6DNS$ $[M+H]^+$ 79.0435, found 79.0437.

2,2'-disulfanediylbis(ethan-2-d-1-amine) dihydrochloride 11

(Compound 647)

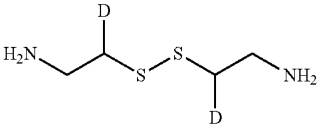

At 0° C., a solution of HCl (4N in 1,4-dioxane, 2.00 mL) was added to a solution of di-tert-butyl (disulfanediylbis (ethane-2,1-diyl-2-d))dicarbamate (9, 50 mg, 0.14 mmol, 1.00 equiv) in methanol (0.5 mL). The reaction was stirred at ambient temperature for 2 h. The reaction was concentrated to get the desired compound in a quantitative yield as a beige powder (32 mg). $^{1}H$ NMR (600 MHz, $D_2O$) δ 3.35 (d, J=6.4 Hz, 4H), 2.95 (t, J=6.4 Hz, 2H) ppm. $^{13}C$ NMR (151 MHz, $D_2O$ (+MeOH as the internal standard) δ 38.20, 33.55 (t, J=21.1 Hz) ppm. HRMS ($ES^+$) calculated for $C_4H_{11}D_2N_2S_2$ $[M+H]^+$ 155.0640, found 155.0645.

Chemical Synthesis of Isotopically Enriched $d_4$-cysteamine and $d_4$-cystamine tert-butyl (2-hydroxyethyl-2,2-$d_2$)carbamate

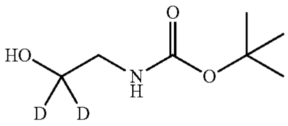

N-Boc-glycine methyl ester (0.100 g, 0.528 mmol, 1.00 equiv) was slowly added to a stirred solution of lithium aluminum deuteride (0.027 g, 0.634 mmol, 1.20 equiv) in anhydrous tetrahydrofuran (1 mL) at 0° C. The mixture was heated at reflux for 3 h and then cooled at 0° C. Ethyl acetate (2 mL) was first added, followed by addition of Rochelle's salt (1 mL). The reaction mixture was stirred at ambient temperature for 1 h, then water was added and the mixture was extracted with ethyl acetate (×3). The combined organic layers were washed with brine (×2), dried over $Na_2SO_4$, filtered and concentrated to give desired compound as a colorless oil in quantitative yield (0.09 g, 0.552 mmol). The compound was used in the next step without further purification. $^{1}H$ NMR (599 MHz, $CDCl_3$) δ 5.15 (s, 1H), 3.24 (d, J=6.0 Hz, 2H), 3.14 (s, 1H), 1.41 (s, 9H) ppm; $^{13}C$ NMR (151 MHz, $CDCl_3$) δ 156.97, 79.75, 43.05, 28.48 ppm; HRMS ($ES^+$) calculated for $C_7H_{13}D_2NO_3Na$ $[M+Na]^+$ 186.1070, found 186.1071.

2-((tert-butoxycarbonyl)amino)ethyl-1,1-$d_2$ 4-methylbenzenesulfonate

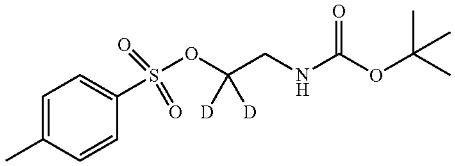 [SMILES: [2H]C([2H])(CNC(=O)OC(C)(C)C)OS(=O)(=O)c1ccc(C)cc1]

At 0° C., p-toluene sulfonyl chloride (0.329 g, 1.73 mmol, 1.46 equiv) and triethylamine (0.322 mL, 2.31 mmol, 1.96 equiv) were added to a solution of tert-butyl (2-hydroxyethyl-2,2-$d_2$)carbamate (0.193 g, 1.18 mmol, 1.00 equiv) in anhydrous dichloromethane (2.1 mL). The reaction was stirred at 0° C. for 10 minutes, then warmed to ambient temperature and stirred for 2 h. The reaction was concentrated and purified by silica gel column chromatography (hexanes/ethyl acetate 80:20) to afford the desired compound as a colorless oil in 51% yield (0.192 g, 0.605 mmol). $^1$H NMR (599 MHz, $CDCl_3$) δ 7.77 (d, J=8.3 Hz, 2H), 7.34 (d, J=8.1 Hz, 2H), 4.88 (s, 1H), 3.35 (d, J=6.0 Hz, 2H), 2.43 (s, 3H), 1.39 (s, 9H) ppm; $^{13}$C NMR (151 MHz, $CDCl_3$) δ 155.72, 145.14, 132.68, 130.06, 128.02, 79.87, 39.66, 28.38, 21.76 ppm; HRMS ($ES^+$) calculated for $C_{14}H_{19}D_2NO_5SNa$ $[M+Na]^+$ 340.1158, found 340.1156.

S-(2-((tert-butoxycarbonyl)amino)ethyl-1,1-$d_2$) ethanethioate

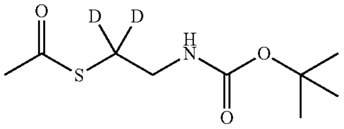 [SMILES: [2H]C([2H])(CNC(=O)OC(C)(C)C)SC(C)=O]

At 0° C., a solution of 2-((tert-butoxycarbonyl)amino) ethyl-1,1-$d_2$ 4-methylbenzenesulfonate (0.160 g, 0.504 mmol, 1.00 equiv) in anhydrous DMF (0.8 mL) was slowly added to a solution of potassium thioacetate (0.115 g, 1.01 mmol, 2.00 equiv) in anhydrous DMF (2.4 mL). The reaction was stirred at 0° C. for 10 minutes, then heated to 50° C. for 90 minutes. The reaction was cooled to ambient temperature and water was added. The mixture was extracted with ethyl acetate (×3). The combined organic layers were washed with water (×2), brine, dried over $Na_2SO_4$, filtered and concentrated. The crude product was purified by silica gel column chromatography (hexanes/EtOAc 80:20) to give the desired compound as a yellow oil in 59% yield (0.066 g; 0.298 mmol). $^1$H NMR (599 MHz, $CDCl_3$) δ 4.81 (s, 1H), 3.28 (d, J=6.2 Hz, 2H), 2.34 (s, 3H), 1.42 (s, 9H) ppm. $^{13}$C NMR (151 MHz, $CDCl_3$) δ 195.93, 155.90, 79.65, 40.22, 30.80, 28.49 ppm; HRMS ($ES^+$) calculated for $C_9H_{15}D_2NO_3SNa$ $[M+Na]^+$ 224.0947, found 224.0948.

Tert-butyl (2-mercaptoethyl-2,2-$d_2$)carbamate

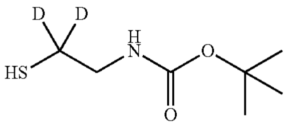

An aqueous solution of sodium hydroxide (10% wt, 1.6 mL) was added to a solution of S-(2-((tert-butoxycarbonyl) amino)ethyl-1,1-$d_2$) ethanethioate (0.126 g, 0.569 mmol, 1 equiv) in methanol (3.0 mL). The reaction was stirred at ambient temperature for 40 minutes. Water was added and the mixture was extracted with ethyl acetate (×3). The combined organic layers were dried over $Na_2SO_4$, filtered and concentrated. The crude reaction was split in two equal parts and one of them purified by silica gel column chromatography (hexanes/EtOAc 80:20 to 70:30) to give the tert-butyl (2-mercaptoethyl-2,2-$d_2$)carbamate as a colourless oil in 43% yield (0.044 mg, 0.245 mmol). HRMS ($ES^+$) calculated for $C_7H_{13}D_2NO_2SNa$ $[M+Na]^+$ 202.0841, found 202.0838. $^1$H NMR (599 MHz, $CDCl_3$) δ 4.95 (s, 1H), 3.28 (d, J=6.3 Hz, 2H), 1.43 (s, 9H) ppm; $^{13}$C NMR (151 MHz, $CDCl_3$) δ 155.87, 79.65, 43.53, 28.49 ppm; HRMS ($ES^+$) calculated for $C_7H_{13}D_2NO_2SNa$ $[M+Na]^+$ 202.0841, found 202.0838.

Di-tert-butyl (disulfanediylbis(ethane-2,1-diyl-2,2-$d_2$))dicarbamate

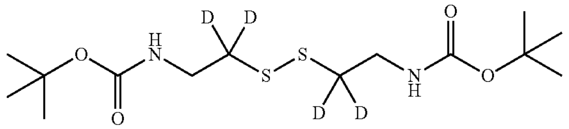 [SMILES: [2H]C([2H])(CNC(=O)OC(C)(C)C)SSC([2H])([2H])CNC(=O)OC(C)(C)C]

Sodium bicarbonate (0.006 g, 0.675 mmol, 1.5 equiv) and iodine (0.007 g, 0.027 mmol, 0.6 equiv) were added portionwise to a solution of tert-butyl (2-mercaptoethyl-2,2-$d_2$) carbamate (0.008 g, 0.045 mmol, 1 equiv) in methanol (0.10 mL). After 5 minutes, a saturated solution of sodium bicarbonate was added and the mixture was extracted with ethyl acetate (×3). The combined organic layers were washed with water, a solution of sodium thiosulfate (10 w.t, 4×2 mL), brine, and dried over $Na_2SO_4$, filtered and concentrated. The crude product was purified by silica gel column chromatography (hexanes/EtOAc 75:25) to afford the title product as a white solid in 25% yield (0.005 g, 0.011 mmol). $^1$H NMR (599 MHz, $CDCl_3$) δ 5.03 (s, 2H), 3.43 (d, J=6.2 Hz, 4H), 1.44 (s, 18H) ppm; $^{13}$C NMR (151 MHz, $CDCl_3$) δ 155.97, 79.71, 39.23, 28.54 ppm; HRMS ($ES^+$) calculated for $C_{14}H_{24}D_4N_2O_4S_2Na$ $[M+Na]^+$ 379.1634, found 379.1630.

2,2'-disulfanediylbis(ethan-2,2-$d_2$-1-aminium) chloride (Compound 655)

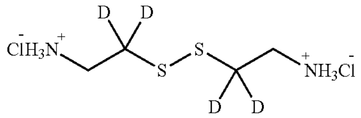

At 0° C., a solution of HCl (4N in 1,4-dioxane, 1.6 mL) was added to a solution of di-tert-butyl (disulfanediylbis (ethane-2,1-diyl-2,2-d2))dicarbamate (0.040 g, 0.112 mmol, 1.00 equiv) in methanol (0.4 mL). The reaction was stirred at ambient temperature for 2 hours. The reaction was concentrated and lyophilized to get the desired compound in a quantitative yield as a white solid (0.025 g, 0.110 mmol). $^1$H NMR (599 MHz, $D_2O$) δ 3.36 (s, 4H) ppm, $^{13}$C NMR (151 MHz, $D_2O$+MeOH as internal standard) δ 37.37 ppm. HRMS ($ES^+$) calculated for $C_4H_9D_4N_2S_2$ $[M+H]^+$ 157.0766, found 157.0769.

2-mercaptoethan-2,2-$d_2$-1-aminium chloride (Compound 656)

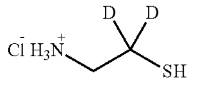

At 0° C., a solution of HCl (4N in 1,4-dioxane, 0.6 mL) was added to a solution of tert-butyl (2-mercaptoethyl-2,2-d2)carbamate (0.015 g, 0.084 mmol, 1.00 equiv) in methanol (0.15 mL). The reaction was stirred at ambient temperature for 2 h. The reaction was concentrated and lyophilized to afford the desired compound in a quantitative yield as a white solid (0.015 g, 0.112 mmol). $^1$H NMR (599 MHz, $D_2O$) δ 3.17 (s, 2H) ppm; $^{13}$C NMR (151 MHz, $D_2O$+MeOH as internal standard) δ 41.67 ppm. HRMS ($ES^+$) calculated for $C_2H_6D_2NS$ $[M+H]^+$ 80.0498, found 80.0498.

Gastric Mucin extract solution: Mucin was prepared as stock solution of 5 mg/mL in water, in NaCl Ringer (150 mM $Na^+$, 4.6 mM $K^+$, 1 mM $Ca^{2+}$, 1 mM $Mg^{2+}$, 150 mM $Cl^-$, 2.5 mM $PO_4^{x-}$ and 10 mM glucose) pH 7.2, and in $HCO_3$-Ringer solution (150 mM $Na^+$, 4.6 mM $K^+$, 1 mM $Ca^{2+}$, 1 mM $Mg^{2+}$, 125 mM 25 mM $HCO_3^-$, 2.5 mM $PO_4^{x-}$ and 10 mM glucose) pH 8.

Cysteamine bitartrate and deuterated cysteamine solutions. Stock solutions of Cysteamine bitartrate or deuterated cysteamine were prepared at a concentration of 40 mM in 1 M acetate buffer pH 4.5 or in $NaHCO_3$-Ringer pH 8. Final concentrations used were between 0-2 mM.

Mucolytic activity on gastric mucin. One hundred microliters of mucin solution were incubated with Cysteamine bitartrate or compound 646 at final concentrations from 0 to 2 mM as indicated in the text. Mixture was incubated at 37° C. for 0-1 hr. Mucolytic activity was ended with 30 microliters of SDS-sample buffer solution. Forty-five microliters of each sample/well were separated in an electrophoresis gel 4-12% Tris-Glycine. After electrophoresis gels were stained with Coomassie Blue solution.

Biological specimens: Isolated native porcine airways were used as experimental model. Sections of open trachea tissue (approx. 2 $cm^2$) were carefully rinsed and cover small volume of $NaHCO_3$-Ringer solution. Mucus secretion was stimulated with Prostaglandin $E_2$ ($PGE_2$, 10−6 M). Secreted mucus over the dissected open airways was carefully collected, aliquoted and immediately frozen at −80° C.

Mucolytic activity on porcine airway mucin: One hundred microliters of collected porcine airway supernatant was incubated with Cysteamine bitartrate or compound 646 at final concentrations from 0 to 2 mM as indicated in the text. Mucolytic activity was ended with 30 microliters of SDS-sample buffer solution. 45 microliters of each sample/well were separated in an electrophoresis gel 4-12% Tris-Glycine. After electrophoresis gels were stained with Coomassie Blue solution.

In vitro mucolytic activity of cysteamine bitartrate and compound 646. To evaluate the mucolytic activity of cysteamine bitartrate and 2-aminoethane-1-d-1-thiol hydrochloride (Compound 646), gastric mucin extract was used as a substrate that was treated with 200 and 400 μM of cysteamine bitartrate or Compound 646 respectively. As shown in FIG. 7, electrophoresis analysis of untreated mucin extract, separated in a 4-12% Tris-Glycine gel, revealed the presence of two major bands (lane 1) that migrated at the level of 50 kDa and around 30 kDa. On the other hand, electrophoresis analysis of mucin extract treated with 200 μM (lane 3) or 400 μM of cysteamine bitartrate showed an important decrease in the protein band visualized at 50 kDa, but not the protein band at 30 kDa. Furthermore, similar changes on the 50 kDa protein band were observed with the gastric mucin samples treated with 200 μM (lane 4) or 400 μM (lane 5) of Compound 646.

Mass spectrometry analysis of the isolated 50 kDa protein band. Muc5ac and Muc6 mucins are two major secretory mucins found in the stomach. In order identify which of these mucins were part of the 50 kDa band, mass spectrometry was utilized. Mass spectrometry analysis of the 50 kDa protein band identified 17 unique peptides that matched with porcine Muc5ac mucin. As shown in FIG. 8, the amino acid residues of the identified peptides were located in two main regions that corresponds to amino acid sequence from 978-1290 and 5176 to 5731.

Mucolytic activity of synthetic compound 646. Respiratory airway mucus contained Muc5aC and Muc5B mucins. In order to determine whether compound 646 be used as a mucolytic agent for respiratory airways, supernatant of mucus collected from porcine airways was treated with compound 646 at different concentration (0-1 mM) for 1 h at 37° C. As shown in FIG. 8 (lane 3 and 4), airway mucus treated with 0.5 and 1 mM Compound 646, two major changes in the proteins at the level of 600 and 200 kDa were observed when compared to untreated airway mucus (lane 1), or airway mucus treated with 0.2 mM of compound 646 (lane 2).

Figure 9:
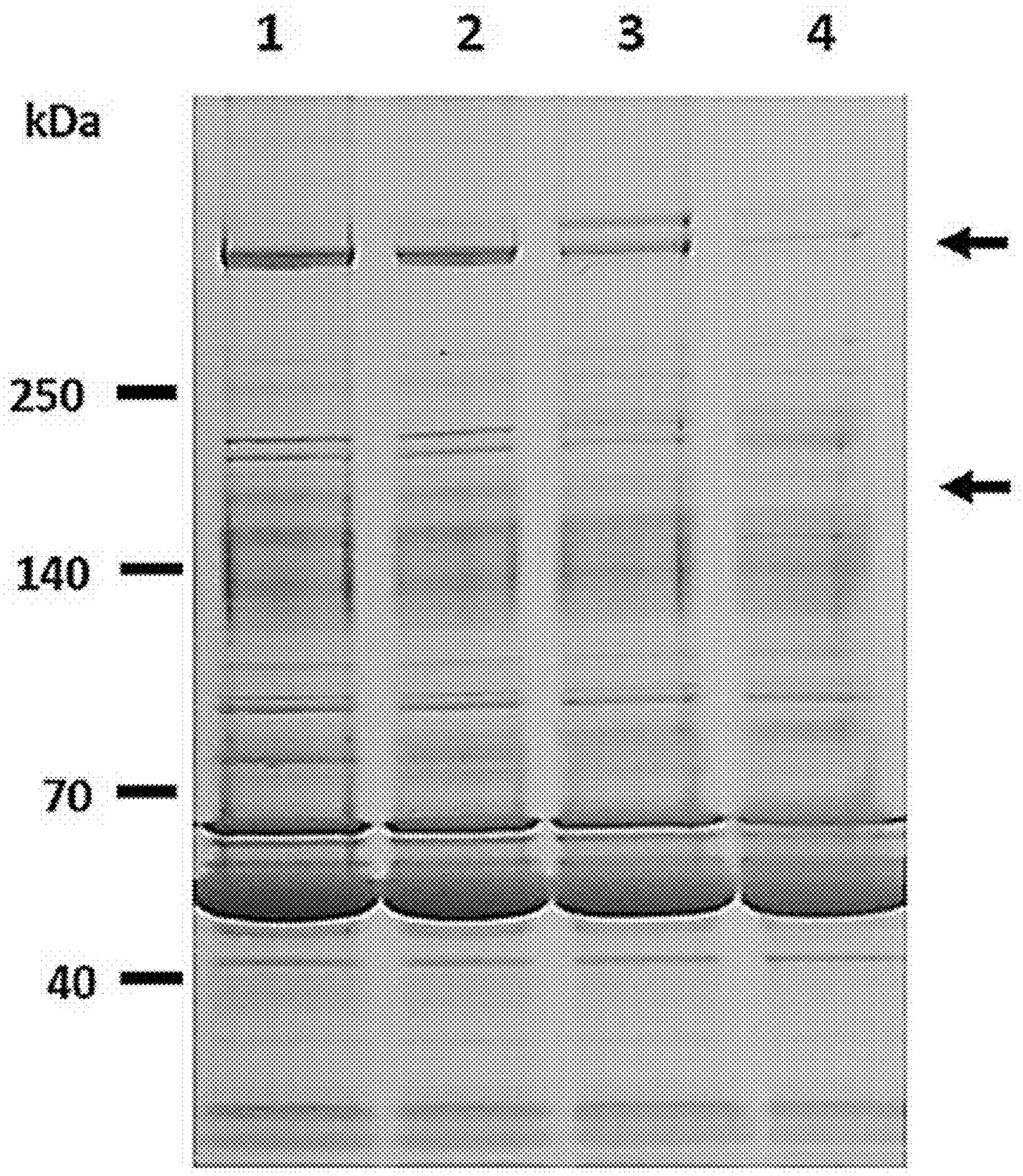
FIG. 9 presents the effect of compound 646 on porcine airway mucus. Mucus collected from porcine upper airways diluted in $NaHCO_3$-Ringer, was treated with different concentrations of compound 646 (0, 0.25. 0.5 and 1 mM), for 60 minutes at 37° C. In lane 1, representative protein pattern after electrophoresis protein separation of untreated porcine airway mucus (40 μg/well). In lane 2, airway mucus treated with 0.25 mM of compound 646 showed similar protein pattern as untreated sample. In contrast, in lane 3 and 4, airway mucus treated with 0.5 mM and 1 mM of compound 646 respectively, showed major changes on two protein bands (black arrows) separated at the level of 600 and 200 kDa approximately.

Mucolytic activity of cysteamine bitartrate under basic and acidic conditions. To validate whether mucolytic activity of cysteamine bitartrate depends on changes of pH, airway mucus supernatant was incubated for 1 h at 37° C. with or without 2 mM cysteamine bitartrate diluted in $NaHCO_3$. An additional airway mucus sample was treated with cysteamine bitartrate and supplemented with 4 μL of 0.1 N of acetic solution pH 4.5. As shown in FIG. 9 (lane 3), airway mucus treated with cysteamine bitartrate under acidic conditions showed also two major changes in the proteins visualized at the level of 600 and 200 kDa, as is also seen with Compound 646. Airway mucus treated with cysteamine bitartrate under basic conditions showed also a reduction of both proteins visualized at 600 and 200 kDa levels (lane 2). The reduction, however, was approximately half of the decrease seen under acidic conditions.

It will be understood that various modifications may be made without departing from the spirit and scope of this disclosure. Accordingly, other embodiments are within the scope of the following claims.

What is claimed:

1. A method for the treatment of a respiratory obstructive disease in a subject in need thereof, comprising administering to the subject a pharmaceutically acceptable composition comprising an effective amount of a compound having the structure of Formula II:

Formula II

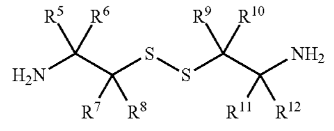

or a pharmaceutically acceptable salt, or solvate thereof, wherein:

$R^5$-$R^{12}$ are independently selected from H or D, and wherein at least one of $R^5$-$R^{12}$ is D, wherein the compound thins and/or loosens the mucus in a respiratory tract wherein the obstructive disease is selected from cystic fibrosis, chronic obstructive pulmonary disease and asthma.

2. The method of claim 1, wherein the compound having a structure of Formula II is selected from:

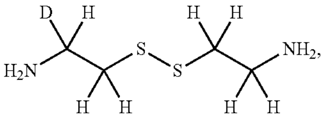,
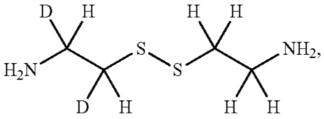,
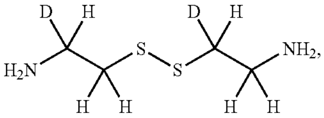,
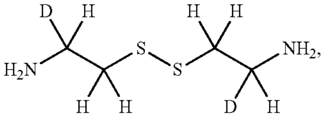,
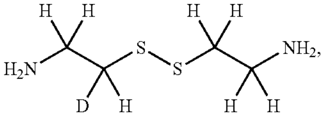,
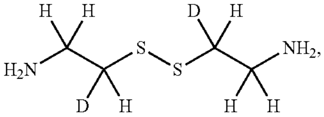,
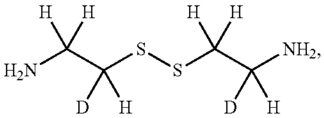,
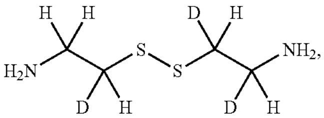,
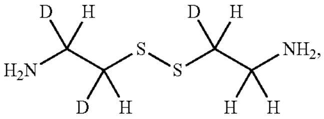,
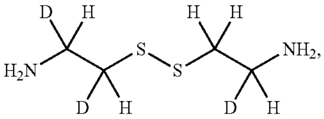,
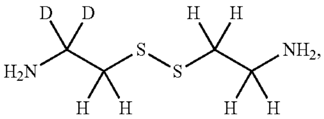,
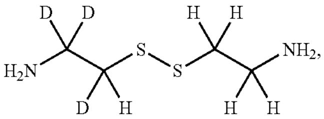, -continued

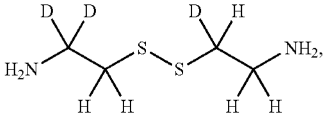,
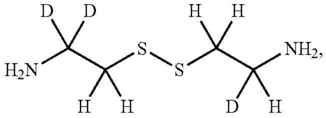,
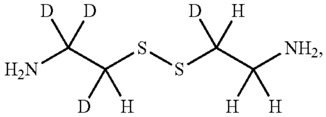,
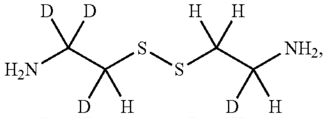,
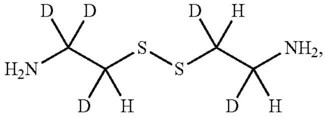,
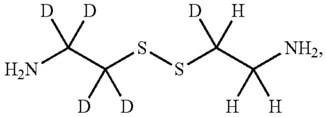,
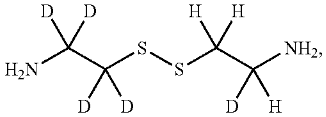,
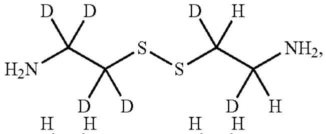,
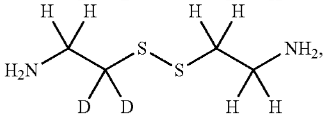,
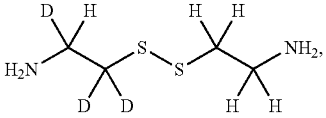,
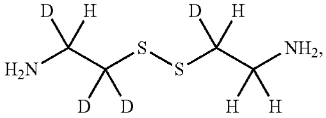,
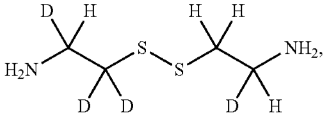,
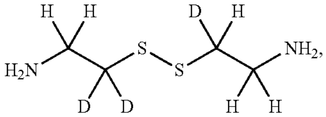,
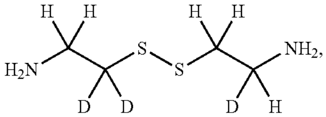,
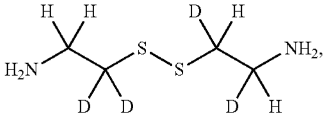, -continued

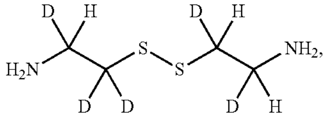

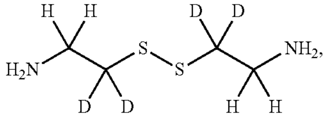

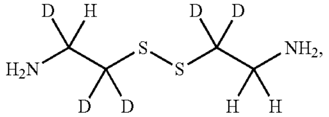

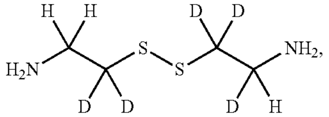

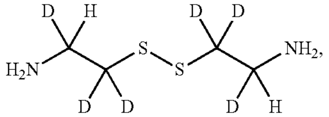

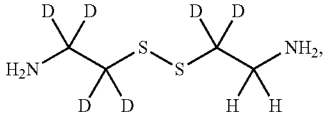

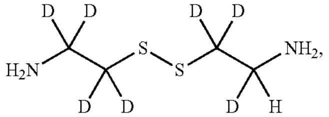

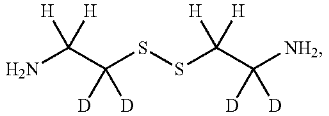

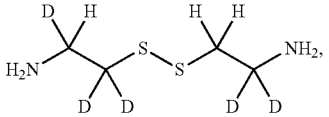

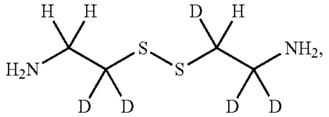

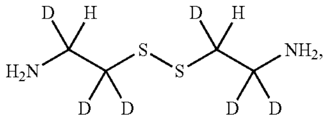

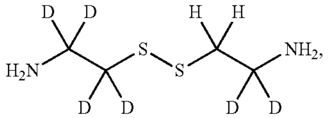

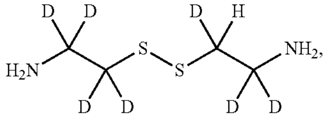

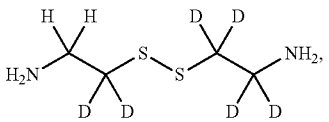

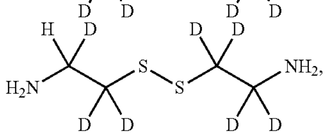

-continued

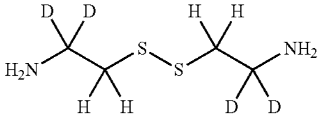

and

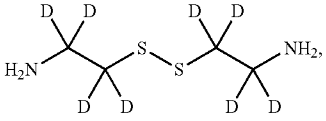

or a pharmaceutically acceptable salt, or solvate thereof.

3. The method of claim 1, wherein the compound having a structure of Formula II is selected from:

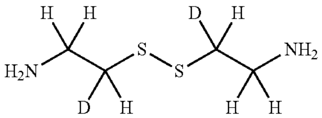

or

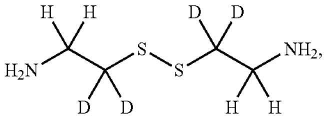

or a pharmaceutically acceptable salt, or solvate thereof.

4. The method of claim 1, wherein the pharmaceutically acceptable composition is formulated for administration by inhalation.

5. The method of claim 1, wherein the pharmaceutically acceptable composition is formulated for administration by a nebulizer.

6. The method of claim 4, wherein the pharmaceutically acceptable composition has a pH from 7 to 9.

7. The method of claim 4, wherein the method further comprises administering by inhalation a second pharmaceutically acceptable composition selected from the group consisting of an agent that has a pH from 4.5 to 6.8, dornase, denufosol, ivacaftor and antibiotics, wherein the second pharmaceutically acceptable composition is administered within a short period time after the administration of the first pharmaceutically acceptable composition.

8. The method of claim 7, wherein the second pharmaceutically acceptable composition is hyperosmolar 3% saline.

9. The method of claim 1, further comprises administering a third pharmaceutically acceptable composition comprising a compound having the structure of Formula I:

Formula I

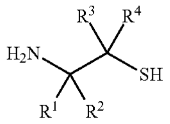

or a pharmaceutically acceptable salt, or solvate thereof, wherein:

$R^1$-$R^4$ are independently selected from H or D, and wherein at least one of $R^1$-$R^4$ is D.

10. The method of claim 9, wherein the compound having the structure of Formula I is selected from the group consisting of:

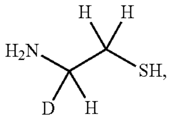
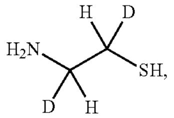
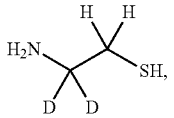
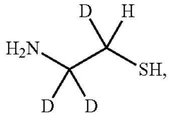
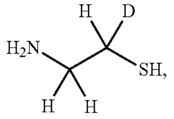
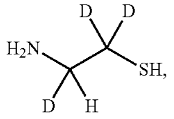
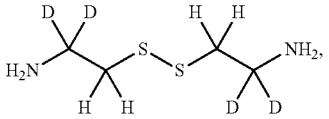

or a pharmaceutically acceptable salt, or solvate thereof.

11. The method of claim 9, wherein the compound is a pharmaceutically acceptable bitartrate salt form of the compound.

12. The method of claim 9, wherein the third pharmaceutically acceptable composition is formulated for oral delivery.

13. The method of claim 12, wherein the third pharmaceutically acceptable composition is formulated for delayed release.

14. The method of claim 12, wherein the third pharmaceutically acceptable composition comprises an enteric coating.

15. The method of claim 9, wherein the composition of Formula II is administered by inhalation in combination, simultaneously or sequentially with systemic administration or oral administration of a compound of formula I or II.

16. The method of claim 15, wherein following inhalation administration of a compound of formula II, a further composition comprising bicarbonate is administered by inhalation to activate or further activate the biological effect of the compound of formula II.

17. A nebulizer or inhaler comprising a compound of Formula II:

Formula II

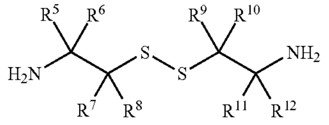

or a pharmaceutically acceptable salt, or solvate thereof, wherein:

$R^5$-$R^{12}$ are independently selected from H or D wherein at least one of $R^5$-$R^{12}$ is D.

18. The nebulizer or inhaler of claim 17, wherein the compound having a structure of Formula II is selected from:

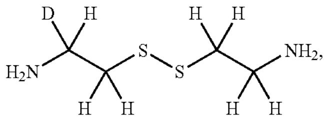
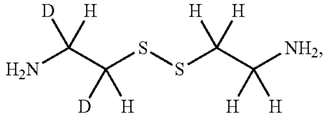

-continued

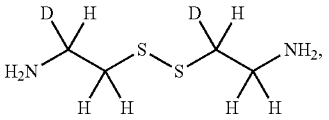
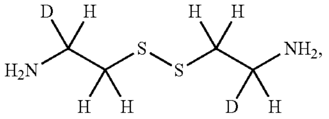
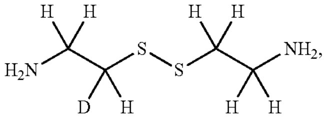
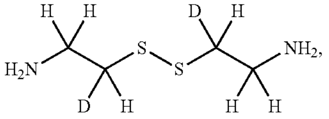
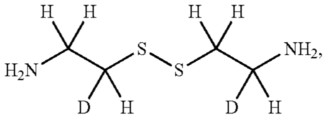
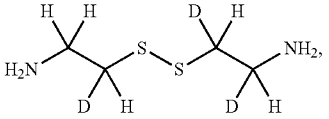
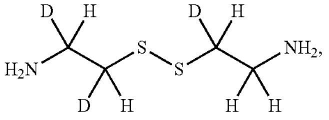
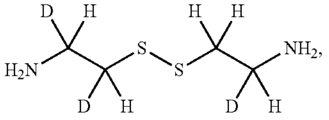
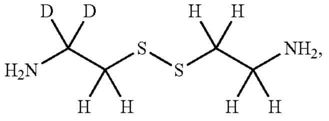
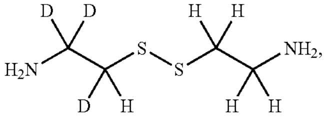
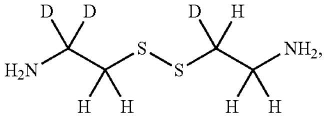
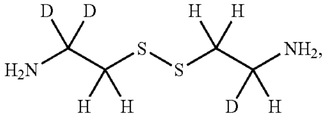
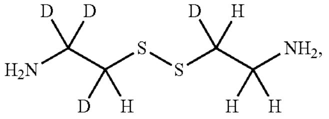
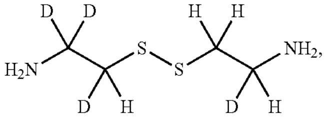

-continued
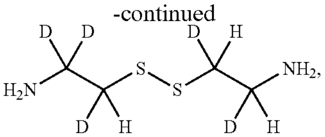
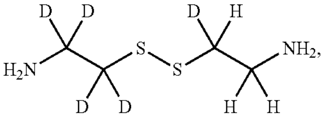
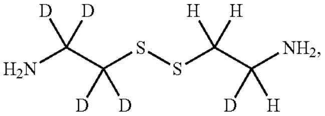
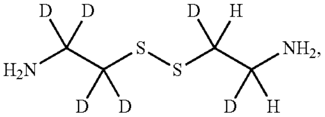
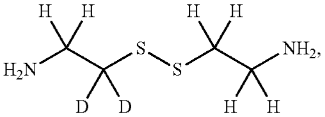
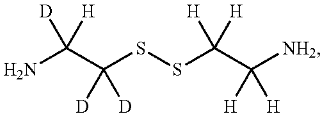
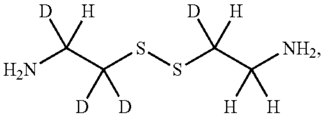
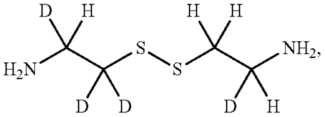
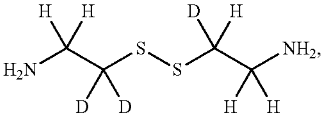
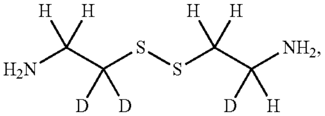
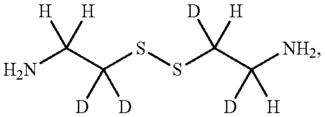
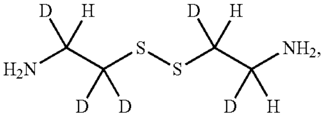
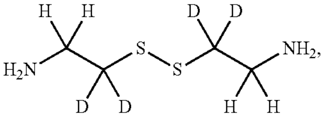
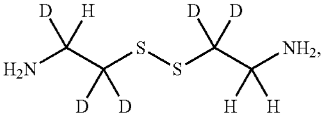
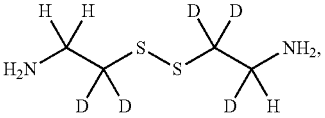
-continued
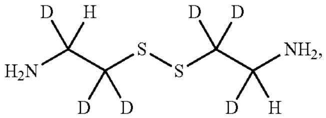
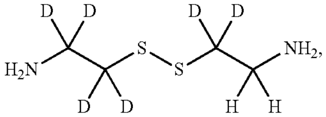
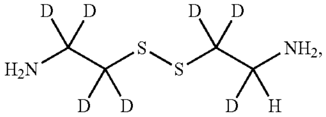
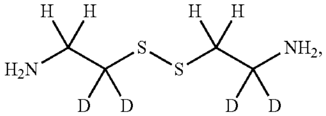
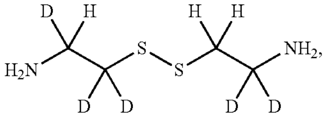
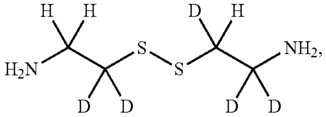
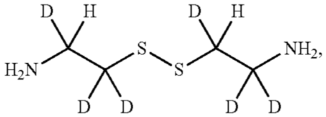
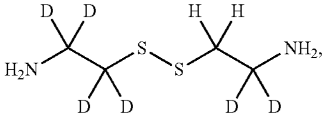
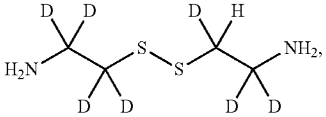
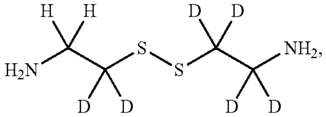
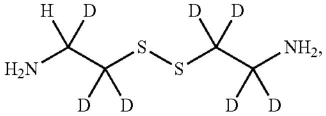
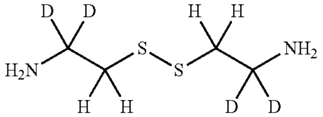
and
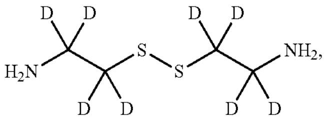
or a pharmaceutically acceptable salt, or solvate thereof.
19. The nebulizer or inhaler of claim 17, wherein the compound having a structure of Formula II is selected from:

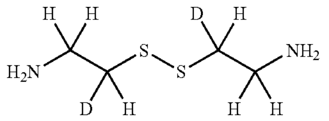
or
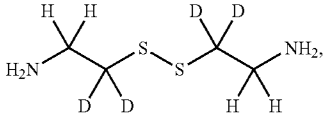
or a pharmaceutically acceptable salt, or solvate thereof.
* * * * *